US012605365B2

(12) United States Patent
Kolla et al.

(10) Patent No.: US 12,605,365 B2
(45) **Date of Patent: *Apr. 21, 2026**

(54) LOSARTAN LIQUID FORMULATIONS AND METHODS OF USE

(71) Applicant: Scienture, LLC, Commack, NY (US)

(72) Inventors: Bhavya Teja Kolla, South Setauket, NY (US); Rahul Surana, Commack, NY (US); Suketu Sanghvi, Kendall Park, NJ (US); Jigar Bhatt, Stony Brook, NY (US)

(73) Assignee: Scienture, LLC, Commack, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,819

(22) Filed: Dec. 5, 2022

(65) Prior Publication Data

US 2023/0414574 A1 Dec. 28, 2023
US 2024/0293371 A9 Sep. 5, 2024

Related U.S. Application Data

(60) Division of application No. 18/052,116, filed on Nov. 2, 2022, now Pat. No. 11,890,273, which is a continuation of application No. PCT/US2021/054054, filed on Oct. 7, 2021.

(60) Provisional application No. 63/089,950, filed on Oct. 9, 2020.

(51) Int. Cl.

| | |
|---|---|
| ***A61K 31/4178*** | (2006.01) |
| ***A61K 9/00*** | (2006.01) |
| ***A61K 9/08*** | (2006.01) |
| ***A61K 9/10*** | (2006.01) |
| ***A61K 9/107*** | (2006.01) |
| ***A61K 47/14*** | (2017.01) |
| ***A61K 47/32*** | (2006.01) |
| ***A61K 47/34*** | (2017.01) |
| ***A61K 47/36*** | (2006.01) |
| ***A61K 47/38*** | (2006.01) |

(52) U.S. Cl.
CPC ........ *A61K 31/4178* (2013.01); *A61K 9/0053* (2013.01); *A61K 9/08* (2013.01); *A61K 9/10* (2013.01); *A61K 9/107* (2013.01); *A61K 47/14* (2013.01); *A61K 47/32* (2013.01); *A61K 47/34* (2013.01); *A61K 47/36* (2013.01); *A61K 47/38* (2013.01)

(58) Field of Classification Search
CPC .............................. A61K 31/4178; A61K 9/10
See application file for complete search history.

(56) References Cited

U.S. PATENT DOCUMENTS

| | | | |
|---|---|---|---|
| 11,890,273 | B2 | 2/2024 | Kolla et al. |
| 12,156,869 | B2 | 12/2024 | Kolla et al. |
| 2006/0160871 | A1 | 7/2006 | Palakodaty et al. |
| 2007/0026026 | A1 | 2/2007 | Delmarre et al. |
| 2018/0280405 | A1 | 10/2018 | Cowen |

FOREIGN PATENT DOCUMENTS

| | | | |
|---|---|---|---|
| CN | 107568236 | * | 1/2018 |
| WO | WO-2009112800 A1 | | 9/2009 |
| WO | WO-2018002673 A1 | | 1/2018 |

OTHER PUBLICATIONS

Yu et al., CN 107568236; published Jan. 12, 2018, English machine translation obtained on Aug. 24, 2024. (Year: 2024).*
International Search Report and Written Opinion for International Application No. PCT/US2021/054054, ISA/US, Commissioner for Patents, Alexandria, Virginia, mailed on Feb. 14, 2022, 11 pages.
Food and Drug Administration, "Cozaar® (losartan potassium) tablets, for oral use," accessdata.fda.gov, Reference ID: 4334171, 21 pages, accessed at https://www.accessdata.fda.gov/drugsatfda_docs/label/2018/020386s0621bl.pdf, United States Food and Drug Administration, United States (Oct. 2018).
Yoshioka, S. and Stella, V.J., "Stability of Drugs and Dosage Forms," Kluwer Academic Publishers, Netherlands (2002).
Office Action mailed Sep. 26, 2023, in U.S. Appl. No. 18/052,116, inventor Kolla, B.T., et al., § 371(c) date Nov. 2, 2022, 19 pages.
Office Action mailed Jun. 20, 2023, in U.S. Appl. No. 18/052,116, inventor Kolla, B.T., et al., § 371(c) date Nov. 2, 2022, 17 pages.
Office Action mailed May 6, 2024, in U.S. Appl. No. 18/421,405, inventor Kolla, B.T., et al., filed Jan. 24, 2024, 16 pages.

* cited by examiner

*Primary Examiner* — Genevieve S Alley
(74) *Attorney, Agent, or Firm* — Sterne, Kessler, Goldstein & Fox P.L.L.C.

(57) ABSTRACT

The present disclosure relates to stable, liquid pharmaceutical compositions of losartan or pharmaceutically acceptable salts thereof for oral administration. The present disclosure further provides powder compositions for reconstitution to provide a liquid formulation. In further aspects, the present disclosure relates to processes for preparation of such pharmaceutical compositions, and methods of treating a subject in need of losartan by administration of a formulation described herein.

20 Claims, 2 Drawing Sheets

LOSARTAN LIQUID FORMULATIONS AND METHODS OF USE

This application is a division of U.S. Nonprovisional patent application Ser. No. 18/052,116, filed on Nov. 2, 2022, which is a continuation of International Application No. PCT/US2021/054054, filed on Oct. 7, 2021, which claims the benefit of U.S. Provisional Patent Application No. 63/089,950, filed on Oct. 9, 2020, each of which is incorporated herein by reference in its entirety.

TECHNICAL FIELD

The present disclosure relates to stable, liquid pharmaceutical compositions of losartan or pharmaceutically acceptable salts thereof for oral administration. The present disclosure further provides powder compositions for reconstitution to provide a liquid formulation. In further aspects, the present disclosure relates to processes for preparation of such pharmaceutical compositions, and methods of treating a subject in need of losartan by administration of a formulation described herein.

BACKGROUND

Hypertension is a serious medical condition wherein the blood pressure of a subject is elevated, increasing the risk of damage to various tissues and organs, including the heart, brain, and kidneys. According to a World Health Organization estimate, as of 2019, 1.13 billion people worldwide experience hypertension.

Losartan is an angiotensin II receptor blocker marketed under the trade name COZAAR®, which is indicated: (1) to lower blood pressure in adults and children greater than 6 years old; (2) to reduce the risk of stroke in patients with hypertension and left ventricular hypertrophy; and (3) to treat diabetic nephropathy with an elevated serum creatinine and proteinuria in patients with type 2 diabetes and a history of hypertension.

COZAAR® is available as 25 mg, 50 mg and 100 mg film coated tablets. A major problem associated with the tablet dosage form is the difficulty in oral administration for patients with swallowing difficulties, e.g., geriatric patients, pediatric patients, patients with neurological disorders, and patients with oral and esophageal cancers. Additionally, patients with underlying disease conditions may experience lower bioavailability from solid dosage forms of losartan.

The prescribing information supplied with COZAAR® describes the preparation of a losartan suspension by dispersing COZAAR® tablets with a suspending agent and a sweetener. This is the only commercially available liquid losartan preparation. However, these compounded preparations can be stored only up to 4 weeks under refrigerated conditions. Additionally, compounded preparations may not be bioequivalent to COZAAR® tablets, which may affect the therapeutic efficacy of such preparations.

Therefore, there remains a need for a stable, liquid pharmaceutical composition of losartan that is safely administrable and bioequivalent to COZAAR® tablets.

BRIEF SUMMARY

Pharmaceutical Composition

In some aspects, the present disclosure provides a pharmaceutical composition comprising losartan or a pharmaceutically acceptable salt thereof and one or more pharmaceutically acceptable excipients, wherein the pharmaceutical composition is suitable for oral administration, liquid, substantially free of impurities, and stable for at least 12 months. In some aspects, the pharmaceutical composition is bioequivalent to COZAAR®. In some aspects, the pharmaceutical composition is not bioequivalent to COZAAR®.

In some aspects, the present disclosure provides a pharmaceutical composition comprising losartan or a pharmaceutically acceptable salt thereof and one or more pharmaceutically acceptable excipients, wherein the pharmaceutical composition is suitable for oral administration, liquid, bioequivalent to COZAAR®, substantially free of impurities, and stable for at least 12 months.

Forms of Losartan

In some aspects, the pharmaceutical composition comprises losartan.

In some aspects, the pharmaceutical composition comprises a pharmaceutically acceptable salt of losartan. In some aspects, the pharmaceutical composition comprises losartan potassium.

Excipients

In some aspects, the pharmaceutical composition comprises two or more pharmaceutically acceptable excipients selected from the group consisting of: a suspending agent, a pH modifying agent, an emulsifying agent, an antioxidant, a chelating agent, a preservative, an antifoaming agent, a solubilizer, a vehicle, a surfactant or wetting agent, a sweetener, a stabilizer, a flavoring agent, and a colorant.

In some aspects, the pharmaceutical composition comprises a crystallization inhibitor or a crystal growth inhibitor. In some aspects, the crystallization inhibitor or crystal growth inhibitor is a polymer. In some aspects, the polymer is polyvinylpyrrolidone. In some aspects, the polymer is polyvinylpyrrolidone K90. In some aspects, the polymer is polyvinylpyrrolidone K30. In some aspects, the polymer is hydroxypropyl methylcellulose. In some aspects, the polymer is polyvinyl acetate. In some aspects, the polymer is a cyclodextrin. In some aspects, the cyclodextrin is hydroxypropyl β-cyclodextrin.

In some aspects, the one or more excipients comprise a suspending agent. In some aspects, the suspending agent is selected from the group consisting of: hydroxyethylcellulose, methylcellulose, hydroxymethylcellulose, hydroxypropylmethylcellulose, microcrystalline cellulose, sodium carboxymethylcellulose, xanthan gum, acacia, an alginate, and guar gum. In some aspects, the suspending agent comprises a thickening agent.

In some aspects, the suspending agent is present in an amount of 0.1 to 15 wt/wt %.

In some aspects, the one or more excipients comprise a pH modifying agent. In some aspects, the pH modifying agent is selected from the group consisting of: citric acid, sodium citrate, acetic acid, sodium acetate, sodium hydroxide, sodium dihydrogen phosphate, and disodium hydrogen phosphate.

In some aspects, the one or more excipients comprise an emulsifying agent selected from the group consisting of: a polysorbate, cetostearyl alcohol, and cetyl alcohol.

In some aspects, the one or more excipients comprise an antioxidant. In some aspects, the antioxidant is selected from the group consisting of: butylated hydroxyanisole, butylated hydroxytoluene, ascorbic acid, tocopherol, and vitamin E.

In some aspects, the pharmaceutical composition comprises an antioxidant in an amount of less than 10 wt/wt %.

In some aspects, the one or more excipients comprise a chelating agent. In some aspects, the chelating agent is ethylenediaminetetraacetic acid. In some aspects, the chelating agent is a disodium salt of ethylenediaminetetraacetic acid.

In some aspects, the one or more excipients comprise a preservative. In some aspects, the preservative is selected from the group consisting of: methyl paraben, ethyl paraben, propyl paraben, butyl paraben, benzoic acid, sodium benzoate, and benzalkonium chloride.

In some aspects, the pharmaceutical composition comprises a preservative in an amount of less than 10 wt/wt %.

In some aspects, the one or more excipients comprise an antifoaming agent. In some aspects, the pharmaceutical composition comprises an antifoaming agent in an amount of less than 10 wt/wt %.

In some aspects, the one or more excipients comprise a solubilizer. In some aspects, the solubilizer is cremophor. In some aspects, the solubilizer is vitamin E. In some aspects, the solubilizer is polyethylene glycol. In some aspects, the solubilizer is propylene glycol. In some aspects, the solubilizer comprises a co-solvent.

In some aspects, the one or more excipients comprise a vehicle. In some aspects, the vehicle is selected from the group consisting of: water, ethanol, glycerol, propylene glycol, polyethylene glycol, and an oil.

In some aspects, the one or more excipients comprise a surfactant or a wetting agent. In some aspects, the surfactant or wetting agent is selected from the group consisting of: a polysorbate, a polyoxamer, and sodium lauryl sulfate.

In some aspects, the one or more excipients comprise a sweetener. In some aspects, the sweetener is selected from the list consisting of: sorbitol, mannitol, xylitol, aspartame, sucralose, saccharine, and acesulfame K.

In some aspects, the pharmaceutical composition comprises a sweetener in an amount of less than 10 wt/wt %.

In some aspects, the one or more excipients comprise a stabilizer.

In some aspects, the one or more excipients comprise a flavoring agent. In some aspects, the flavoring agent is selected from the list consisting of: an apple flavoring agent, an orange flavoring agent, a mint flavoring agent, a cherry flavoring agent, and a strawberry flavoring agent.

In some aspects, the pharmaceutical composition comprises a flavoring agent in an amount of less than 10 wt/wt %.

In some aspects, the one or more excipients comprise a colorant.

Free from Impurities

In some aspects, the pharmaceutical composition comprises less than 5 wt/wt % of all impurities relative to the mass of losartan.

In some aspects, the pharmaceutical composition comprises less than 5 wt/wt % of an impurity relative to the mass of losartan.

In some aspects, the impurity is a product of losartan oxidation.

In some aspects, the impurity is a product of losartan degradation.

In some aspects, the impurity is a side product of a method of losartan synthesis.

In some aspects, the impurity is a byproduct of a method of losartan synthesis.

In some aspects, the impurity is losartan carboxylic acid.

In some aspects, the impurity is losartan impurity D. In some aspects, the pharmaceutical composition comprises less than 5 wt/wt % of losartan impurity D relative to the mass of losartan. In some aspects, the pharmaceutical composition comprises about 0.01 to 5 wt/wt % of losartan impurity D relative to the mass of losartan. In some aspects, the pharmaceutical composition comprises about 0.1 to 5 wt/wt % of losartan impurity D relative to the mass of losartan.

In some aspects, the impurity is losartan impurity E. In some aspects, the pharmaceutical composition comprises less than 5 wt/wt % of losartan impurity E relative to the mass of losartan. In some aspects, the pharmaceutical composition comprises about 0.01 to 5 wt/wt % of losartan impurity E relative to the mass of losartan. In some aspects, the pharmaceutical composition comprises about 0.1 to 5 wt/wt % of losartan impurity E relative to the mass of losartan.

In some aspects, the impurity is a biological contaminant. In some aspects, the impurity is a living biological contaminant. In some aspects, the impurity is a dead biological contaminant. In some aspects, the impurity is a viral contaminant. In some aspects, the impurity is a fungal contaminant. In some aspects, the impurity is a bacterial contaminant. In some aspects, the impurity is a bacterial endotoxin.

In some aspects, the biological contaminant is a replication-competent, metabolically inactive or minimally active biological product. In some aspects, the replication-competent, metabolically inactive or minimally active biological product is a spore.

In some aspects, the impurity is pyrogenic.

In some aspects, the impurity is detectable as visible particulate matter.

Sterility

In some aspects, the pharmaceutical composition has been subjected to a sterilizing treatment. In some aspects, one or more components of the pharmaceutical composition have been subjected to a sterilizing treatment.

In some aspects, the sterilizing treatment comprises filtration. In some aspects, the sterilizing treatment comprises exposure to a high temperature. In some aspects, the sterilizing treatment comprises exposure to a low temperature. In some aspects, the sterilizing treatment comprises application of ultraviolet radiation. In some aspects, the sterilizing treatment is sufficient to kill a living biological contaminant.

Stability

In some aspects, the pharmaceutically acceptable composition is stable as measured by one or more substantially unchanged characteristics after storage, the one or more substantially unchanged characteristics selected from the group consisting of: the concentration of losartan in the pharmaceutical composition; the concentration of an impurity in the pharmaceutical composition; the visual appearance of the pharmaceutical composition; the viscosity of the pharmaceutical composition; the uniformity of the pharmaceutical composition; and the sedimentation rate of the pharmaceutical composition.

In some aspects, the pharmaceutical composition is stable at 2° C.-8° C. and ≤65% relative humidity. In some aspects, the pharmaceutical composition is stable for 3 months at 2° C.-8° C. and ≤65% relative humidity. In some aspects, the pharmaceutical composition is stable for 4 months at 2° C.-8° C. and ≤65% relative humidity. In some aspects, the pharmaceutical composition is stable for 6 months at 2° C.-8° C. and ≤65% relative humidity. In some aspects, the pharmaceutical composition is stable for 8 months at 2° C.-8° C. and ≤65% relative humidity. In some aspects, the pharmaceutical composition is stable for 10 months at 2° C.-8° C. and ≤65% relative humidity. In some aspects, the pharmaceutical composition is stable for 12 months at 2° C.-8° C. and ≤65% relative humidity. In some aspects, the pharmaceutical composition is stable for 16 months at 2°

C.-8° C. and ≤65% relative humidity. In some aspects, the pharmaceutical composition is stable for 18 months at 2° C.-8° C. and ≤65% relative humidity. In some aspects, the pharmaceutical composition is stable for 24 months at 2° C.-8° C. and ≤65% relative humidity.

In some aspects, the pharmaceutical composition is stable at 15° C.-25° C. and ≤65% relative humidity. In some aspects, the pharmaceutical composition is stable for 3 months at 15° C.-25° C. and ≤65% relative humidity. In some aspects, the pharmaceutical composition is stable for 4 months at 15° C.-25° C. and ≤65% relative humidity. In some aspects, the pharmaceutical composition is stable for 6 months at 15° C.-25° C. and ≤65% relative humidity. In some aspects, the pharmaceutical composition is stable for 8 months at 15° C.-25° C. and ≤65% relative humidity. In some aspects, the pharmaceutical composition is stable for 10 months at 15° C.-25° C. and ≤65% relative humidity. In some aspects, the pharmaceutical composition is stable for 12 months at 15° C.-25° C. and ≤65% relative humidity. In some aspects, the pharmaceutical composition is stable for 16 months at 15° C.-25° C. and ≤65% relative humidity. In some aspects, the pharmaceutical composition is stable for 18 months at 15° C.-25° C. and ≤65% relative humidity. In some aspects, the pharmaceutical composition is stable for 24 months at 15° C.-25° C. and ≤65% relative humidity.

In some aspects, the pharmaceutical composition is stable at 30° C. and ≤65% relative humidity. In some aspects, the pharmaceutical composition is stable for 3 months at 30° C. and ≤65% relative humidity. In some aspects, the pharmaceutical composition is stable for 4 months at 30° C. and ≤65% relative humidity. In some aspects, the pharmaceutical composition is stable for 6 months at 30° C. and ≤65% relative humidity. In some aspects, the pharmaceutical composition is stable for 8 months at 30° C. and ≤65% relative humidity. In some aspects, the pharmaceutical composition is stable for 10 months at 30° C. and ≤65% relative humidity. In some aspects, the pharmaceutical composition is stable for 12 months at 30° C. and ≤65% relative humidity. In some aspects, the pharmaceutical composition is stable for 16 months at 30° C. and ≤65% relative humidity. In some aspects, the pharmaceutical composition is stable for 18 months at 30° C. and ≤65% relative humidity. In some aspects, the pharmaceutical composition is stable for 24 months at 30° C. and ≤65% relative humidity.

In some aspects, the pharmaceutical composition is stable at 40° C. and 75% relative humidity. In some aspects, the pharmaceutical composition is stable for 3 months at 40° C. and 75% relative humidity. In some aspects, the pharmaceutical composition is stable for 4 months at 40° C. and 75% relative humidity. In some aspects, the pharmaceutical composition is stable for 6 months at 40° C. and 75% relative humidity. In some aspects, the pharmaceutical composition is stable for 8 months at 40° C. and 75% relative humidity. In some aspects, the pharmaceutical composition is stable for 10 months at 40° C. and 75% relative humidity. In some aspects, the pharmaceutical composition is stable for 12 months at 40° C. and 75% relative humidity. In some aspects, the pharmaceutical composition is stable for 16 months at 40° C. and 75% relative humidity. In some aspects, the pharmaceutical composition is stable for 18 months at 40° C. and 75% relative humidity. In some aspects, the pharmaceutical composition is stable for 24 months at 40° C. and 75% relative humidity.

Liquid and Powder Forms

In some aspects, the pharmaceutical composition of the present disclosure is a solution, an emulsion, or a suspension. In some aspects, the present disclosure provides for a concentrated form of losartan or a pharmaceutically acceptable salt thereof, which can be combined with a suitable diluent to prepare a pharmaceutical composition described herein. In some aspects, the concentrated form of losartan or a pharmaceutically acceptable salt thereof is selected from the group consisting of: a powder, a plurality of granules, modified losartan, and a concentrated liquid form (e.g., a concentrated solution or a low-volume mixed solid and liquid phase). In some aspects, the concentrated form of losartan or a pharmaceutically acceptable salt thereof can be combined with a suitable diluent to prepare one or more of a solution, a suspension, and an emulsion.

In some aspects, the concentrated form of losartan or a pharmaceutically acceptable salt thereof is combined with the suitable diluent and heated to form a pharmaceutically acceptable composition disclosed herein. In some aspects, the concentrated form of losartan or a pharmaceutically acceptable salt thereof is combined with the suitable diluent and an additional component to form a pharmaceutically acceptable composition disclosed herein. In some aspects, the additional component is a pH modifying agent. In some aspects, the pH modifying agent is an acid. In some aspects, the pH modifying agent is a base.

Solution

In some aspects, the pharmaceutical composition is a solution. In some aspects, the pharmaceutical composition is a solution and the pharmaceutical composition comprises losartan. In some aspects, the pharmaceutical composition is a solution and the pharmaceutical composition comprises a pharmaceutically acceptable salt of losartan. In some aspects, the pharmaceutical composition is a solution and the pharmaceutical composition comprises losartan potassium.

In some aspects, the pharmaceutical composition is a solution comprising losartan substantially dissolved in a pharmaceutically acceptable vehicle. In some aspects, the solution comprises at least 75% of losartan or pharmaceutically acceptable salt thereof in dissolved form. In some aspects, the solution comprises at least 90% of losartan or pharmaceutically acceptable salt thereof in dissolved form.

In some aspects, the solution further comprises one or more inactive ingredients selected from the group consisting of: co-solvents, pH modifying agents, surfactants, antioxidants, preservatives, and flavoring agents.

Emulsion

In some aspects, the pharmaceutical composition is an emulsion. In some aspects, the pharmaceutical composition is an emulsion and the pharmaceutical composition comprises losartan. In some aspects, the pharmaceutical composition is an emulsion and the pharmaceutical composition comprises a pharmaceutically acceptable salt of losartan. In some aspects, the pharmaceutical composition is an emulsion and the pharmaceutical composition comprises losartan potassium.

In some aspects, the emulsion is a multiple emulsion. In some aspect, the emulsion is a microemulsion.

In some aspects, the emulsion comprises at least two immiscible liquid phases wherein one liquid phase is in the form of globules. In some aspects, the pharmaceutical composition comprises an emulsifying agent. In some aspects, the pharmaceutical composition is an emulsion wherein a hydrophobic phase comprises at least 50% of losartan or a pharmaceutically acceptable salt thereof. In some aspects, the pharmaceutical composition is an emulsion wherein a hydrophobic phase comprises at least 60% of losartan or a pharmaceutically acceptable salt thereof. In some aspects, the pharmaceutical composition is an emulsion wherein a hydrophobic phase comprises at least 70% of losartan or a pharmaceutically acceptable salt thereof. In some aspects, the pharmaceutical composition is an emulsion wherein a hydrophobic phase comprises at least 80% of losartan or a pharmaceutically acceptable salt thereof. In some aspects, the pharmaceutical composition is an emulsion wherein a hydrophobic phase comprises at least 90% of losartan or a pharmaceutically acceptable salt thereof.

Suspension

In some aspects, the pharmaceutical composition is a suspension. In some aspects, the pharmaceutical composition is a suspension and the pharmaceutical composition comprises losartan. In some aspects, the pharmaceutical composition is a suspension and the pharmaceutical composition comprises a pharmaceutically acceptable salt of losartan. In some aspects, the pharmaceutical composition is a suspension and the pharmaceutical composition comprises losartan potassium.

In some aspects, the suspension is a cloudy biphasic liquid comprising a plurality of losartan particles uniformly dispersed in a pharmaceutically acceptable vehicle. In some aspects, at least 50% of losartan or pharmaceutically acceptable salt thereof is in suspended form. In some aspects, at least 60% of losartan or pharmaceutically acceptable salt thereof is in suspended form. In some aspects, at least 70% of losartan or pharmaceutically acceptable salt thereof is in suspended form. In some aspects, at least 80% of losartan or pharmaceutically acceptable salt thereof is in suspended form. In some aspects, at least 90% of losartan or pharmaceutically acceptable salt thereof is in suspended form.

In some aspects, the suspension comprises a flocculating agent.

Powder

In some aspects, the present disclosure provides a powder which is combined with a liquid to produce the pharmaceutical composition described herein.

In some aspects, the powder comprises losartan or a pharmaceutically acceptable salt thereof. In some aspects, the powder comprises losartan. In some aspects, the powder comprises losartan potassium.

In some aspects, the powder comprises one or more pharmaceutically acceptable excipients.

In some aspects, the losartan powder is bioequivalent to COZAAR®.

In some aspects, the powder is sterile.

In some aspects, the powder is non-pyrogenic.

In some aspects, the powder is substantially free of impurities.

In some aspects, the liquid is a solvent. In some aspects, the solvent is water.

In some aspects, the liquid is provided in a container. In some aspects, the container is a bottle. In some aspects, the bottle is an amber bottle.

In some aspects, the container contains a suspending agent. In some aspects, the container contains a preservative. In some aspects, the container contains a sweetener. In some aspects, the container contains a flavoring agent.

In some aspects, the powder is packaged in a sachet.

Granules

In some aspects, the present disclosure provides a plurality of granules which is combined with a liquid to produce the pharmaceutical composition described herein.

In some aspects, the plurality of granules comprises losartan or a pharmaceutically acceptable salt thereof. In some aspects, the plurality of granules comprises losartan. In some aspects, the plurality of granules comprises losartan potassium.

In some aspects, the plurality of granules comprises one or more pharmaceutically acceptable excipients.

In some aspects, the plurality of granules is bioequivalent to COZAAR®.

In some aspects, the plurality of granules is sterile.

In some aspects, the plurality of granules is non-pyrogenic.

In some aspects, the plurality of granules is substantially free of impurities.

In some aspects, the liquid is a solvent. In some aspects, the solvent is water.

In some aspects, the liquid is provided in a container. In some aspects, the container is a bottle. In some aspects, the bottle is an amber bottle.

In some aspects, the container contains a suspending agent. In some aspects, the container contains a preservative. In some aspects, the container contains a sweetener. In some aspects, the container contains a flavoring agent.

In some aspects, the plurality of granules is packaged in a sachet.

Particle Characterization

In some aspects, the suspension or the powder exhibits a dissolution profile as measured using a paddle type apparatus. In some aspects, the dissolution profile is measured at 50 rpm. In some aspects, the dissolution profile of the suspension or powder is measured in a mixture of water and 0.1N HCl. In some aspects, less than 35% of the plurality of losartan particles are dissolved in 15 minutes. In some aspects, less than 70% of the plurality of losartan particles are dissolved in 30 minutes. In some aspects, at least 80% of the plurality of losartan particles are dissolved in 60 minutes. In some aspects, at least 80% of the plurality of losartan particles are dissolved in 15 minutes. In some aspects, at least 85% of the plurality of losartan particles are dissolved in 15 minutes. In some aspects, at least 90% of the plurality of losartan particles are dissolved in 15 minutes. In some aspects, at least 95% of the plurality of losartan particles are dissolved in 15 minutes. In some aspects, about 100% of the plurality of losartan particles are dissolved in 15 minutes. In some aspects, at least 80% of the plurality of losartan particles are dissolved in 5 minutes. In some aspects, at least 85% of the plurality of losartan particles are dissolved in 5 minutes. In some aspects, at least 90% of the plurality of losartan particles are dissolved in 5 minutes. In some aspects, at least 95% of the plurality of losartan particles are dissolved in 5 minutes. In some aspects, about 100% of the plurality of losartan particles are dissolved in 5 minutes.

In some aspects, the suspension or powder exhibits a particle size distribution as measured using a particle size analyzer. In some aspects, the particle size analyzer is a Malvern Mastersizer particle size analyzer. In some aspects, the particle size analyzer is a Malvern Mastersizer 3000 particle size analyzer. In some aspects, the particle size analyzer is a Malvern Zetasizer particle size analyzer.

In some aspects, the particle size distribution comprises a D10 value less than 100 μm. In some aspects, the particle size distribution comprises a D50 value less than 500 μm. In some aspects, the particle size distribution comprises a D90 value less than 1000 μm. In some aspects, the particle size distribution comprises a D10 value less than 100 μm, a D50 value less than 500 μm, and a D90 value less than 1000 μm.

In some aspects, the particle size distribution comprises a D10 value less than 20 μm. In some aspects, the particle size distribution comprises a D50 value less than 100 μm. In some aspects, the particle size distribution comprises a D90 value less than 300 μm. In some aspects, the particle size distribution comprises a D10 value less than 20 μm, a D50 value less than 100 μm, and a D90 value less than 300 μm.

In some aspects, the particle size distribution comprises a D10 value less than 2 μm. In some aspects, the particle size distribution comprises a D50 value less than 10 μm. In some aspects, the particle size distribution comprises a D90 value less than 30 μm. In some aspects, the particle size distribution comprises a D10 value less than 2 μm, a D50 value less than 10 μm, and a D90 value less than 30 μm.

In some aspects, the particle size distribution comprises a D10 value less than 100 nm. In some aspects, the particle size distribution comprises a D50 value less than 500 nm. In some aspects, the particle size distribution comprises a D90 value less than 1000 nm. In some aspects, the particle size distribution comprises a D10 value less than 100 nm, a D50 value less than 500 nm, and a D90 value less than 1000 nm.

In some aspects, the particle size distribution comprises a D90 value less than 2 μm. In some aspects, the particle size distribution comprises a D90 value less than 1 μm. In some aspects, the particle size distribution comprises a D90 value less than 500 nm.

In some aspects, the particle size distribution comprises a D10 value less than or equal to 1 μm. In some aspects, the particle size distribution comprises a D50 value less than or equal to 5 μm. In some aspects, the particle size distribution comprises a D90 value less than or equal to 15 μm. In some aspects, the particle size distribution comprises a D10 value less than or equal to 1 μm, a D50 value less than or equal to 5 μm, and a D90 value less than or equal to 15 μm.

In some aspects, the suspension or the powder has a sedimentation rate of less than 10% over a period of 24 hours. In some aspects, the suspension or the powder has a sedimentation rate of less than 5% over a period of 24 hours.

Modified Losartan

In some aspects, the pharmaceutical composition comprises a modified losartan. In some aspects, the powder comprises a modified losartan. In some aspects, the modified losartan comprises losartan or a pharmaceutically acceptable salt thereof complexed or coated with a wax, one or more polymers, or one or more other inactive ingredients. In some aspects, the modified losartan comprises losartan or a pharmaceutically acceptable salt thereof complexed or coated with a wax. In some aspects, the modified losartan comprises losartan or a pharmaceutically acceptable salt thereof complexed or coated with one or more polymers. In some aspects, the modified losartan is losartan or a pharmaceutically acceptable salt thereof coated with one or more inactive ingredients.

Crystalline Form

In some aspects, the powder or suspension comprises losartan or a pharmaceutically acceptable salt thereof in crystalline form. In some aspects, the crystalline form is thermodynamically stable. In some aspects, the crystalline form is thermodynamically stable, as measured by a substantially unchanged X-ray powder diffraction (XRPD) profile following storage. In some aspects, the crystalline form is thermodynamically stable, as measured by a substantially unchanged differential scanning calorimetry (DSC) profile following storage.

Concentration of Losartan

In some aspects, the pharmaceutical composition comprises about 1 mg/mL to about 50 mg/mL of losartan or pharmaceutically acceptable salt thereof. In some aspects, the pharmaceutical composition comprises about 2 mg/mL to about 20 mg/mL of losartan or a pharmaceutically acceptable salt thereof. In some aspects, the pharmaceutical composition comprises about 5 mg/mL to about 20 mg/mL of losartan or a pharmaceutically acceptable salt thereof. In some aspects, the pharmaceutical composition comprises about 8 mg/mL to about 12 mg/mL of losartan or a pharmaceutically acceptable salt thereof.

pH

In some aspects, the pharmaceutical composition has a pH between 2 and 10. In some aspects, the pharmaceutical composition has a pH between 2 and 7. In some aspects, the pharmaceutical composition has a pH of about 6. In some aspects, the pharmaceutical composition has a pH of about 4. In some aspects, the pharmaceutical composition has a pH of 4.2. In some aspects, the pharmaceutical composition has a pH of about 5. In some aspects, the pharmaceutical composition has a pH less than 6. In some aspects, the pharmaceutical composition has a pH greater than 6. In some aspects, the pharmaceutical composition has a pH between 7 and 9. In some aspects, the pharmaceutical composition has a pH between 3 and 5. In some aspects, the pharmaceutical composition has a pH between 5 and 7.

Pharmacokinetic Parameters and Bioequivalence

In some aspects, the mean $T_{max}$ of the pharmaceutical composition described herein is about 98% to about 102% of the mean $T_{max}$ of COZAAR®. In some aspects, the mean $T_{max}$ of the pharmaceutical composition described herein is about 95% to about 105% of the mean $T_{max}$ of COZAAR®. In some aspects, the mean $T_{max}$ of the pharmaceutical composition described herein is about 90% to about 110% of the mean $T_{max}$ of COZAAR®. In some aspects, the mean $T_{max}$ of the pharmaceutical composition described herein is about 80% to about 125% of the mean $T_{max}$ of COZAAR®. In some aspects, the mean $T_{max}$ of the pharmaceutical composition described herein is about 75% to about 130% of the mean $T_{max}$ of COZAAR®. In some aspects, the mean $T_{max}$ of the pharmaceutical composition described herein is about 70% to about 135% of the mean $T_{max}$ of COZAAR®. In some aspects, the mean $T_{max}$ of the pharmaceutical composition described herein is about 65% to about 140% of the mean $T_{max}$ of COZAAR®. In some aspects, the mean $T_{max}$ of the pharmaceutical composition described herein is about 60% to about 145% of the mean $T_{max}$ of COZAAR®. In some aspects, the mean $T_{max}$ of the pharmaceutical composition described herein is about 60%, about 65%, about 70%, about 75%, about 80%, about 85%, about 90%, about 95%, about 100%, about 105%, about 110%, about 115%, about 120% about 125%, about 130%, about 135%, about 140%, or about 145% of the mean $T_{max}$ of COZAAR®.

In some aspects, the mean $T_{max}$ of the pharmaceutical composition described herein is about 50% to about 150% of the mean $T_{max}$ of COZAAR®. In some aspects, the mean $T_{max}$ of the pharmaceutical composition described herein is about 40% to about 160% of the mean $T_{max}$ of COZAAR®. In some aspects, the mean $T_{max}$ of the pharmaceutical composition described herein is about 30% to about 170% of the mean $T_{max}$ of COZAAR®. In some aspects, the mean $T_{max}$ of the pharmaceutical composition described herein is about 20% to about 200% of the mean $T_{max}$ of COZAAR®.

In some aspects, the mean $C_{max}$ of the pharmaceutical composition described herein is about 98% to about 102% of the mean $C_{max}$ of COZAAR®. In some aspects, the mean $C_{max}$ of the pharmaceutical composition described herein is about 95% to about 105% of the mean $C_{max}$ of COZAAR®. In some aspects, the mean $C_{max}$ of the pharmaceutical composition described herein is about 90% to about 110% of the mean $C_{max}$ of COZAAR®. In some aspects, the mean $C_{max}$ of the pharmaceutical composition described herein is about 80% to about 125% of the mean $C_{max}$ of COZAAR®.

In some aspects, the mean $C_{max}$ of the pharmaceutical composition described herein is about 75% to about 130% of the mean $C_{max}$ of COZAAR®. In some aspects, the mean $C_{max}$ of the pharmaceutical composition described herein is about 70% to about 135% of the mean $C_{max}$ of COZAAR®. In some aspects, the mean $C_{max}$ of the pharmaceutical composition described herein is about 65% to about 140% of the mean $C_{max}$ of COZAAR®. In some aspects, the mean $C_{max}$ of the pharmaceutical composition described herein is about 60% to about 145% of the mean $C_{max}$ of COZAAR®. In some aspects, the mean $C_{max}$ of the pharmaceutical composition described herein is about 60%, about 65%, about 70%, about 75%, about 80%, about 85%, about 90%, about 95%, about 100%, about 105%, about 110%, about 115%, about 120% about 125%, about 130%, about 135%, about 140%, or about 145% of the mean $C_{max}$ of COZAAR®.

In some aspects, the mean $AUC_{0-\infty}$ of the pharmaceutical composition described herein is about 98% to about 102% of the mean $AUC_{0-\infty}$ of COZAAR®. In some aspects, the mean $AUC_{0-\infty}$ of the pharmaceutical composition described herein is about 95% to about 105% of the mean $AUC_{0-\infty}$ of COZAAR®. In some aspects, the mean $AUC_{0-\infty}$ of the pharmaceutical composition described herein is about 90% to about 110% of the mean $AUC_{0-\infty}$ of COZAAR®. In some aspects, the mean $AUC_{0-\infty}$ of the pharmaceutical composition described herein is about 80% to about 125% of the mean $AUC_{0-\infty}$ of COZAAR®. In some aspects, the mean $AUC_{0-\infty}$ of the pharmaceutical composition described herein is about 75% to about 130% of the mean $AUC_{0-\infty}$ of COZAAR®. In some aspects, the mean $AUC_{0-\infty}$ of the pharmaceutical composition described herein is about 70% to about 135% of the mean $AUC_{0-\infty}$ of COZAAR®. In some aspects, the mean $AUC_{0-\infty}$ of the pharmaceutical composition described herein is about 65% to about 140% of the mean $AUC_{0-\infty}$ of COZAAR®. In some aspects, the mean $AUC_{0-\infty}$ of the pharmaceutical composition described herein is about 60% to about 145% of the mean $AUC_{0-\infty}$ of COZAAR®. In some aspects, the mean $AUC_{0-\infty}$ of the pharmaceutical composition described herein is about 60%, about 65%, about 70%, about 75%, about 80%, about 85%, about 90%, about 95%, about 100%, about 105%, about 110%, about 115%, about 120% about 125%, about 130%, about 135%, about 140%, or about 145% of the mean $AUC_{0-\infty}$ of COZAAR®.

Additional Active Ingredients

In some aspects, the pharmaceutical composition comprises one or more active ingredients in addition to losartan or a pharmaceutically acceptable salt thereof. In some aspects, the one or more active ingredients are selected from the group consisting of: calcium channel blockers, diuretics, ACE inhibitors, and beta blockers. In some aspects, the one or more active ingredients are calcium channel blockers. In some aspects, the one or more active ingredients are diuretics. In some aspects, the one or more active ingredients are ACE inhibitors. In some aspects, the one or more active ingredients are beta blockers.

Viscosity

In some aspects, the pharmaceutical composition has a viscosity of less than 2000 centipoise, as measured using a Brookfield viscometer. In some aspects, the pharmaceutical composition has a viscosity of less than 1000 centipoise, as measured using a Brookfield viscometer.

Volume

In some aspects, the pharmaceutical composition is administered in a volume of 0.5 mL to 50 mL. In some aspects, the pharmaceutical composition is administered in a volume of less than 100 mL. In some aspects, the pharmaceutical composition is administered in a volume of about 2.5 mL, about 5 mL, or about 10 mL.

Container

In some aspects, a pharmaceutical composition is packaged in a glass container. In some aspects, the powder is packaged in a glass container. In some aspects, the glass container is an amber glass container. In some aspects, the amber glass container is child resistant. In some aspects, the amber glass container comprises a child resistant cap. In some aspects, the pharmaceutical composition is packaged in a polymeric container. In some aspects, the polymeric container is child resistant. In some aspects, the polymeric container comprises a child resistant cap. In some aspects, the polymeric container comprises high density polyethylene (HDPE). In some aspects, the polymeric container comprises low density polyethylene (LDPE).

Kit

In some aspects, the present disclosure provides for a kit comprising a pharmaceutically acceptable composition described herein, and further comprising a set of instructions for administration of the pharmaceutically acceptable composition to a subject in need thereof. In some aspects, the set of instructions comprises an instruction to add an amount of a diluent to a container comprising a concentrated form of losartan or a pharmaceutically acceptable salt thereof, wherein the kit comprises the container. In some aspects, the diluent is water.

In some aspects, the present disclosure provides for a kit comprising: a concentrated form of losartan or a pharmaceutically acceptable salt thereof; a diluent; and a set of instructions, wherein the set of instructions comprises: instructions for combining the concentrated form of losartan or a pharmaceutically acceptable salt thereof and the diluent to form a pharmaceutically acceptable composition described herein; and instructions for administration of the pharmaceutically acceptable composition to a subject in need thereof. In some aspects, the concentrated form of losartan or a pharmaceutically acceptable salt thereof is in the form of a powder or a plurality of granules.

In some aspects, the kit comprises a concentrated form of a pharmaceutical composition disclosed herein. In some aspects, the concentrated form is prepared by combining components of a pharmaceutical composition disclosed herein without dilution to a final concentration suitable for administration to a subject. In some aspects, the concentrated form is a concentrated liquid form. In some aspects, the concentrated liquid form is a solution. In some aspects, the concentrated liquid form is a suspension. In some aspects, the concentrated form is a dry form. In some aspects, the dry form comprises less than 0.1%, 0.5%, 1%, 2%, 3%, 4%, 5%, 6%, 7%, 8%, 9%, or 10% of water by weight of the dry form. In some aspects, the dry form is a powder or a plurality of granules.

Method of Preparing Suspension

In some aspects, the present disclosure provides a method of preparing a suspension described herein, the method comprising combining a plurality of losartan particles and a suspending agent. In some aspects, the plurality of losartan particles is combined with the suspending agent.

In some aspects, the present disclosure provides a method of preparing a suspension described herein, the method comprising dissolving losartan or a pharmaceutically acceptable salt thereof in a suitable fluid (e.g., water), adjusting the pH of the suitable liquid comprising losartan or a pharmaceutically acceptable salt thereof, and combining the suitable liquid comprising losartan or a pharmaceutically acceptable salt thereof with the remaining components of the suspension, thereby forming the suspension.

In some aspects, the present disclosure provides a method of preparing a suspension described herein, the method comprising combining losartan or a pharmaceutically acceptable salt thereof and one or more excipients, granulating the composition with a suitable fluid (e.g., water), drying the resulting composition to form a dry composition, and combining the dry composition with a suitable liquid, thereby forming the suspension.

In some aspects, the present disclosure provides a method of preparing a suspension described herein, the method comprising a step of particle size reduction. In some aspects, the step of particle size reduction comprises wet milling. In some aspects, the step of particle size reduction comprises microfluidization. In some aspects, the step of particle size reduction comprises homogenization. In some aspects, the step of particle size reduction comprises nano-milling.

In some aspects, a pH modifying agent is added after the plurality of losartan particles is combined with the suspending agent. In some aspects, the pH modifying agent is selected from the group consisting of: citric acid, sodium citrate, acetic acid, sodium acetate, sodium hydroxide, dibasic calcium phosphate, sodium dihydrogen phosphate, and disodium hydrogen phosphate. In some aspects, the pH modifying agent is a buffer.

In some aspects, the one or more polymers are sprayed by dissolving the one or more polymers in a volatile solvent. In some aspects, the volatile solvent is selected from the group consisting of: ethanol, acetone, or isopropyl alcohol. In some aspects, the volatile solvent is ethanol. In some aspects, the volatile solvent is acetone. In some aspects, the volatile solvent is isopropyl alcohol.

In some aspects, heated air is added to cause evaporation of the volatile solvent. In some aspects, evaporation of the volatile solvent causes deposition of the one or more polymers onto the surface of a particle comprising losartan or a pharmaceutically acceptable salt thereof. In some aspects, the particles comprising losartan or a pharmaceutically acceptable salt thereof are dried to form a modified losartan. In some aspects, the plurality of losartan particles is provided as a modified losartan which is preformed. In some aspects, the plurality of losartan particles comprises losartan or a pharmaceutically acceptable salt thereof.

In some aspects, the plurality of losartan particles is fluidized in a fluidized bed system, and are then coated with one or more polymers. In some aspects, the plurality of losartan particles comprises losartan or a pharmaceutically acceptable salt thereof. In some aspects, the plurality of losartan particles has a particle size of less than 1000 μm. In some aspects, the plurality of losartan particles has a particle size of less than 750 μm. In some aspects, the plurality of losartan particles has a particle size of less than 500 μm. In some aspects, the plurality of losartan particles has a particle size of less than 250 μm.

In some aspects, the one or more polymers comprise pH dependent polymers (e.g., Eudragit L, Eudragit S, or cellulose acetate phthalate) and/or pH independent polymers (e.g., Eudragit RS, Eudragit RL, or cellulose acetate).

In some aspects, the modified losartan tastes less bitter than losartan.

In some aspects, the modified losartan is more stable than losartan.

Method of Preparing Solution or Emulsion

In some aspects, the present disclosure provides a method of preparing a solution or an emulsion described herein, comprising combining the components of the solution or the emulsion.

In some aspects, losartan or a pharmaceutically acceptable salt thereof is dissolved in a hydrophobic phase (e.g., vegetable oil). In some aspects, an antioxidant is added to a hydrophobic phase. In some aspects, the hydrophobic phase comprising losartan or a pharmaceutically acceptable salt thereof is mixed with a hydrophilic phase. In some aspects, the hydrophilic phase comprises a sweetener. In some aspects, the hydrophilic phase comprises a flavoring agent. In some aspects, the hydrophilic phase comprises Polysorbate 80 and/or Tweens. In some aspects, the emulsion is prepared by combining and mixing the hydrophobic phase and the hydrophilic phase. In some aspects, the hydrophobic phase and hydrophilic phase are mixed at a high speed using a homogenizer.

Method of Preparing Powder

In some aspects, the present disclosure provides a method of preparing a powder, the method comprising dry blending the components of a pharmaceutical composition described herein. In some aspects, the pharmaceutical composition is a suspension described herein.

Method of Preparing Modified Losartan

In some aspects, the present disclosure provides a method of preparing modified losartan, the method comprising complexing or coating losartan or a pharmaceutically acceptable salt thereof with a substance, wherein the substance is a wax, a polymer, or one or more other inactive ingredients. In some aspects, the modified losartan is formed during preparation of the pharmaceutical composition. In some aspects, modified losartan is formed by complexation with an ion exchange resin. In some aspects, modified losartan is formed by complexation with a cyclodextrin. In some aspects, the modified losartan is prepared by microencapsulation of losartan or a pharmaceutically acceptable salt thereof in a coat of inactive ingredients.

Method of Treatment

In some aspects, the present disclosure provides a method of treating a subject in need thereof comprising administering to the subject a therapeutically effective amount of the pharmaceutical composition described herein.

In some aspects, the subject has been diagnosed with pre-hypertension or hypertension. In some aspects, the subject has been diagnosed with pre-hypertension. In some aspects, the subject has been diagnosed with hypertension. In some aspects, the subject has a history of hypertension.

In some aspects, the subject has been diagnosed with left ventricular hypertrophy. In some aspects, the subject has been diagnosed with both hypertension and left ventricular hypertrophy.

In some aspects, the subject has been diagnosed with type 2 diabetes.

In some aspects, the subject has been diagnosed with nephropathy.

In some aspects, the subject has been diagnosed with diabetic nephropathy.

In some aspects, the subject has been diagnosed with proteinuria.

In some aspects, the subject exhibits a urinary albumin to creatinine ratio of greater than or equal to 300 mg/g.

In some aspects, the subject has been diagnosed with an elevated serum creatinine.

In some aspects, the pharmaceutical composition is co-administered with at least one other pharmaceutical agent. In some aspects, the at least one pharmaceutical agent is an antihypertensive agent. In some aspects, the antihypertensive agent is selected from the group consisting of: an angiotensin II antagonist, an angiotensin converting enzyme inhibitor, or a neutral endopeptidase/angiotensin converting enzyme inhibitor. In some aspects, the antihypertensive agent is an angiotensin II antagonist. In some aspects, the antihypertensive agent is an angiotensin converting enzyme inhibitor. In some aspects, the antihypertensive agent is a neutral endopeptidase/angiotensin converting enzyme inhibitor.

DEFINITIONS

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present disclosure, suitable methods and materials are described below. The materials, methods and examples are illustrative only and are not intended to be limiting. Other features and advantages of the disclosure will be apparent from the detailed description and from the claims.

In order to further define this disclosure, the following terms and definitions are provided.

The singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "pharmaceutically acceptable" as used herein refers to those compounds, materials, compositions, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "modified losartan" as used herein refers to losartan or a pharmaceutically acceptable salt thereof, wherein losartan or a pharmaceutically acceptable salt thereof is complexed or coated with inactive ingredients. In some aspects, a modified losartan is more stable than losartan or a pharmaceutically acceptable salt thereof not complexed or coated with inactive ingredients. In some aspects, a suspension comprising a modified losartan is more stable than a suspension comprising losartan or a pharmaceutically acceptable salt thereof not complexed or coated with inactive ingredients. In some aspects, a modified losartan is less soluble in water than losartan or a pharmaceutically acceptable salt thereof not complexed or coated with inactive ingredients. In some aspects, a modified losartan is more resistant to degradation or oxidation than losartan or a pharmaceutically acceptable salt thereof not complexed or coated with inactive ingredients.

The term "excipient" refers to any substance, not itself a therapeutic agent, which may be used in a composition for delivery of an active therapeutic agent to a subject or combined with an active therapeutic agent (e.g., to create a pharmaceutical composition) to improve its handling or storage properties or to permit or facilitate formation of a dose unit of the composition (e.g., formation of a hydrogel which may then be optionally incorporated into a patch). Excipients include, but are not limited to, solvents, penetration enhancers, wetting agents, antioxidants, lubricants, emollients, substances added to improve appearance or texture of the composition and substances used to form hydrogels. Any such excipients can be used in any dosage forms according to the present disclosure. The foregoing classes of excipients are not meant to be exhaustive but merely illustrative as a person of ordinary skill in the art would recognize that additional types and combinations of excipients could be used to achieve the desired goals for delivery of a drug. The excipient can be an inert substance, an inactive substance, and/or a not medicinally active substance. The excipient can serve various purposes. A person skilled in the art can select one or more excipients with respect to the particular desired properties by routine experimentation and without any undue burden. The amount of each excipient used can vary within ranges conventional in the art. Techniques and excipients which can be used to formulate dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

The term "effective amount" or "pharmaceutically effective amount" or "therapeutically effective amount" as used herein refers to the amount or quantity of a drug (e.g., losartan or a pharmaceutically acceptable salt thereof) or pharmaceutically active substance which is sufficient to elicit the required or desired therapeutic response, or in other words, the amount which is sufficient to elicit an appreciable biological response when administered to a patient.

The term "unit dosage form" or "unit dose composition" as used herein refers to a device containing a quantity of the therapeutic compound, said quantity being such that one or more predetermined units may be provided as a single therapeutic administration.

The term "$C_{max}$" as used herein refers to the maximum plasma concentration of a drug after administration of the drug.

The term "$T_{max}$" as used herein refers to the time required to reach the maximal plasma concentration $C_{max}$ after administration of a drug.

The term "AUC" as used herein refers to the area under the curve of a plot of plasma concentration versus time following administration of a drug.

The term "$AUC_{0-t}$" as used herein refers to the area under the drug concentration-time curve from time zero to the time of the last measurable concentration ($C_t$).

The term "$AUC_{0-\infty}$" as used herein refers to the area under the drug concentration-time curve from time zero to infinity.

The term "steady state" as used herein means that the amount of the drug reaching the system is approximately the same as the amount of the drug leaving the system. Thus, at "steady-state," the patient's body eliminates the drug at approximately the same rate that the drug becomes available to the patient's system through absorption into the blood stream.

The term "mean" refers to an average value in a patient population. For example, a "mean $C_{max}$" refers to an average of the maximum plasma concentrations of a drug in a patient population.

The term "treating" or "treatment" as used herein refers to the administration of a composition to a subject for therapeutic purposes.

The term "serum concentration" generally refers to the amount of a drug or other compound in the circulation, both bound to proteins and unbound, the latter of which generally corresponds to the therapeutically active fraction.

The term "bioavailability" generally refers to the rate and extent to which the active ingredient is absorbed from a drug product and becomes available at the site of action.

"Bioequivalence" is a term in pharmacokinetics generally used to assess the expected in vivo biological equivalence of two proprietary preparations of a drug. Two pharmaceutical products are bioequivalent if they are pharmaceutically equivalent and their bioavailabilities (rate and extent of availability) after administration in the same molar dose are similar to such a degree that their effects, with respect to both efficacy and safety, can be expected to be essentially the same. Bioequivalence criteria include The United States Food and Drug Administration ("FDA") requirement for bioequivalence studies to have percentage ratios of the test vs reference for $C_{max}$ and AUC, at 90% confidence interval, between 80% and 125%.

The term "stable" as used herein means a composition is substantially unchanged after storage for a period of time under given storage conditions. In some aspects, a composition is "stable" if it meets the International Council for Harmonisation of Technical Requirements for Pharmaceuticals for Human Use (ICH) requirements for stability. In some aspects, a composition is considered stable if after a period of at least 12 months of storage at 15° C.-25° C. and ≤65% relative humidity, the concentration or integrity of carrier components or losartan or a pharmaceutically acceptable salt thereof is substantially unchanged (e.g., a loss of no more than 1%, 2%, 3%, 4%, 5%, 6%, 7%, 8%, 9%, or 10% of losartan or a pharmaceutically acceptable salt thereof). Stability can also be analyzed by subjecting composition to accelerated stability conditions for a shorter period of time (e.g., 6 months at 30° C. at 65% relative humidity, or 6 months at 40° C. and 75% relative humidity) and observing no substantial change in the concentration of losartan or a pharmaceutically acceptable salt thereof, or other components in the composition. In some aspects, a pharmaceutical composition is considered "stable" if it exhibits substantially the same characteristics before and after storage at a given temperature and relative humidity over a given time, wherein the characteristics are one or more of: the concentration of losartan or a pharmaceutically acceptable salt thereof, the concentration of an impurity, the appearance of the composition, the viscosity of the composition, the uniformity of the dosage form, or the sedimentation rate of the composition (for suspension products). In some aspects, the pharmaceutical composition is substantially free of impurities following storage.

As used herein, the terms "impurity" and "impurities" refer to any chemical entities (e.g., product of losartan oxidation or degradation) or microbial entities (e.g., a living or dead microbial species) present in a pharmaceutical composition described herein, other than the disclosed components of the pharmaceutical composition. In some aspects, an impurity is a change in the physical properties and/or chemical structure of losartan or a pharmaceutically acceptable salt thereof, due to exposure to heat, oxidation, excipients, and/or time under storage. An impurity can alter the pharmacokinetic properties of the pharmaceutical composition (e.g., where the impurity is a chemical derivative of losartan or a pharmaceutically acceptable salt thereof), the stability of the pharmaceutical composition, or the safety of administration of the pharmaceutical composition (e.g., where the impurity is a pathogenic or pyrogenic microbial contaminant). In some aspects, the impurity is a side product or byproduct of a method of losartan synthesis. In some aspects, an impurity is a product of losartan oxidation or degradation, indicating a decrease in losartan dosage, or formation of a chemical entity having a different bioavailability than losartan. In some aspects, the impurity is a pyrogenic microbial entity or product of a microbial entity.

As used herein, the term "wt/wt %" refers to the percentage, by mass, of a component of a pharmaceutical composition described herein, relative to the mass of the entire pharmaceutical composition, unless otherwise specified (as in the case of "wt/wt % relative to the mass of losartan"). For example, if a component is described as 10 wt/wt %, the mass of the component is 10% of the mass of the entire composition including the component.

As used herein, "wt/wt % relative to the mass of losartan" refers to the percentage, by mass, of a component of a pharmaceutical composition described herein, relative to the mass of losartan present in the pharmaceutical composition. For example, if an impurity is described as "less than 2 wt/wt % relative to the mass of losartan", the mass of the impurity present in the pharmaceutical composition is less than 2% of the mass of losartan present in the pharmaceutical composition. It will be understood by a person of ordinary skill in the art to which this application pertains that "the mass of losartan" in this context refers to the mass of losartan, and does not include the counterions of a salt of losartan (e.g., if losartan in the form of losartan potassium is added to form a composition).

As used herein, the term "wt/vol %" refers to the percentage, by mass, of a component of a liquid pharmaceutical composition described herein, relative to the volume of the entire liquid pharmaceutical composition, where the ratio corresponds to a number of grams of the component in a 100 mL volume. For example, if a component is described as 10 wt/vol %, the ratio of the mass of the component relative to the volume of the liquid pharmaceutical composition is that of 100 mL of a liquid composition containing 10 grams of the component.

The term "losartan" refers to 2-butyl-4-chloro-1-((2'-(1H-tetrazol-5-yl) (1,1'-biphenyl)-4-yl) methyl)-1H-imidazole-5-methanol, having the following chemical structure:

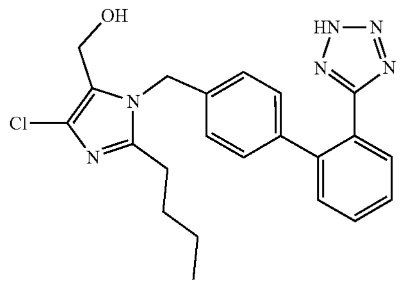 [SMILES: CCCCc1nc(Cl)c(CO)n1Cc1ccc(-c2ccccc2-c2nn[nH]n2)cc1]

The term "losartan impurity D" refers to 2-butyl-4-chloro-5-formylimidazole, also known as 2-butyl-5-chloro-1H-imidazole-4-carboxaldehyde, having the following chemical structure:

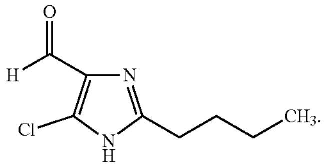 [SMILES: CCCCc1nc(C=O)c(Cl)[nH]1]

The term "losartan impurity E" refers to 5-(4'-methylbiphenyl-2-yl)-1H-tetrazole, having the following chemical structure:

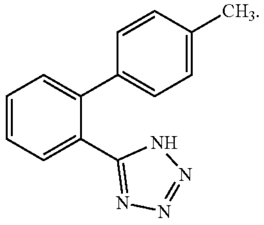 [SMILES: Cc1ccc(-c2ccccc2-c2nnn[nH]2)cc1]

Losartan is marketed as a losartan potassium salt tablet formulation under the trade name COZAAR®.

As used herein, the term "sedimentation rate" refers to the rate at which a suspended phase of a suspension settles to the surface of the container.

As used herein, the term "liquid" when referring to a pharmaceutical composition herein refers to a composition which is substantially a liquid. Liquid compositions of the present disclosure include suspensions, which are substantially liquid, despite comprising solid particles suspended in a liquid phase.

As used herein, the term "multiple emulsion" refers to a liquid composition comprising both oil-in-water and water-in-oil type emulsions.

As used herein, the term "microemulsion" refers to a thermodynamically stable emulsion. In some aspects, a microemulsion is transparent or slightly turbid. In some aspects, the dispersed phase of a microemulsion consists of small droplets with a diameter of about 100 Å to about 1,000 Å.

The terms "co-administration", "co-administering", or "co-administered" refer to administering a combination of therapeutic agents, such as, for example, a combination of losartan and an anti-hypertensive drug. The combination can be administered as two separate entities, such as, for example, in separate dosage forms, or as a single combination entity, such as, for example, in the same oral, liquid pharmaceutical composition. One therapeutic agent (e.g., losartan or a pharmaceutically acceptable salt form thereof) can be administered before, concomitantly, or subsequently to the administering of the other therapeutic agent (e.g., an anti-hypertensive drug) to the subject.

DETAILED DESCRIPTION OF THE INVENTION

Pharmaceutical Composition

Figure 1:
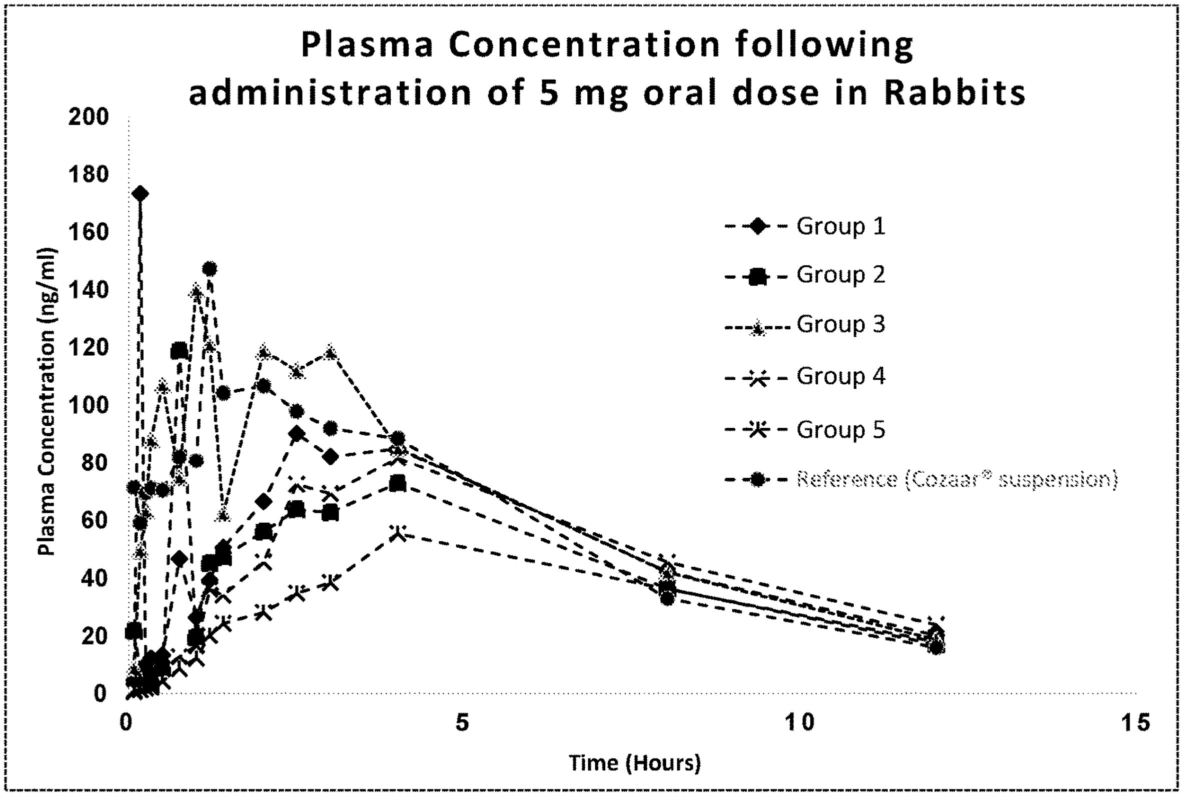
FIG. 1 shows the plasma concentration of losartan following administration of 5 mg oral dose of losartan potassium in rabbits, as described in Example 15. Corresponding losartan pharmacokinetic parameters are summarized in Table 13.

In some aspects, the present disclosure provides a pharmaceutical composition comprising losartan or a pharmaceutically acceptable salt thereof and one or more pharmaceutically acceptable excipients, wherein the pharmaceutical composition is suitable for oral administration, liquid, substantially free of impurities, and stable for at least 12 months. In some aspects, the pharmaceutical composition is bioequivalent to COZAAR®. In some aspects, the pharmaceutical composition is not bioequivalent to COZAAR®.

In some aspects, the present disclosure provides a pharmaceutical composition comprising losartan or pharmaceutically acceptable salt thereof and one or more pharmaceutically acceptable excipients, wherein the pharmaceutical composition is suitable for oral administration, liquid, bioequivalent to COZAAR®, substantially free of impurities, and stable for at least 12 months.

Forms of Losartan

In some aspects, the pharmaceutical composition comprises losartan.

In some aspects, the pharmaceutical composition comprises a pharmaceutically acceptable salt of losartan. In some aspects, the pharmaceutical composition comprises losartan potassium. In some aspects, the pharmaceutical composition comprises a sodium salt of losartan. In some aspects, the pharmaceutical composition comprises a lithium salt of losartan.

Excipients

In some aspects, the pharmaceutical composition comprises one or more pharmaceutically acceptable excipients selected from the group consisting of: a suspending agent, a pH modifying agent, an emulsifying agent, an antioxidant, a chelating agent, a preservative, an antifoaming agent, a solubilizer, a vehicle, a surfactant or wetting agent, a sweetener, a stabilizer, a flavoring agent, and a colorant. In some aspects, the pharmaceutical composition comprises two or more pharmaceutically acceptable excipients selected from the group consisting of: a suspending agent, a pH modifying agent, an emulsifying agent, an antioxidant, a chelating agent, a preservative, an antifoaming agent, a solubilizer, a vehicle, a surfactant or wetting agent, a sweetener, a stabilizer, a flavoring agent, and a colorant.

In some aspects, the pharmaceutical composition comprises a crystallization inhibitor or a crystal growth inhibitor. In some aspects, the crystallization inhibitor or crystal growth inhibitor is a polymer. In some aspects, the polymer is polyvinylpyrrolidone. In some aspects, the polymer is polyvinylpyrrolidone K90. In some aspects, the polymer is polyvinylpyrrolidone K30. In some aspects, the polymer is hydroxypropyl methylcellulose. In some aspects, the polymer is polyvinyl acetate. In some aspects, the polymer is a cyclodextrin. In some aspects, the cyclodextrin is hydroxypropyl β-cyclodextrin.

In some aspects, the one or more excipients comprise a suspending agent. In some aspects, the suspending agent is selected from the group consisting of: hydroxyethylcellulose, methylcellulose, hydroxymethylcellulose, hydroxypropylmethylcellulose, microcrystalline cellulose, sodium carboxymethylcellulose, xanthan gum, acacia, an alginate, and guar gum. In some aspects, the suspending agent is hydroxyethylcellulose.

In some aspects, the suspending agent is methylcellulose. In some aspects, the suspending agent is hydroxymethylcellulose. In some aspects, the suspending agent is hydroxypropylmethylcellulose. In some aspects, the suspending agent is microcrystalline cellulose. In some aspects, the suspending agent is sodium carboxymethylcellulose. In some aspects, the suspending agent is xanthan gum. In some aspects, the suspending agent is acacia. In some aspects, the suspending agent is an alginate. In some aspects, the suspending agent is guar gum. In some aspects, the suspending agent comprises a thickening agent.

In some aspects, the suspending agent is present in an amount of 0.1 to 15 wt/wt %. In some aspects, the suspending agent is present in an amount of 0.5 to 10 wt/wt %. In some aspects, the suspending agent is present in an amount of 1 to 8 wt/wt %. In some aspects, the suspending agent is present in an amount of 2 to 7 wt/wt %. In some aspects, the suspending agent is present in an amount of 3 to 6 wt/wt %. In some aspects, the suspending agent is present in an amount of about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, or about 15 wt/wt %.

In some aspects, the suspending agent is present in an amount of 0.1 to 15 wt/vol %. In some aspects, the suspending agent is present in an amount of 0.5 to 10 wt/vol %. In some aspects, the suspending agent is present in an amount of 1 to 8 wt/vol %. In some aspects, the suspending agent is present in an amount of 2 to 7 wt/vol %. In some aspects, the suspending agent is present in an amount of 3 to 6 wt/vol %. In some aspects, the suspending agent is present in an amount of about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, or about 15 wt/vol %.

In some aspects, the one or more excipients comprise a pH modifying agent. In some aspects, the pH modifying agent is selected from the group consisting of: citric acid, sodium citrate, sodium hydroxide, sodium dihydrogen phosphate, and disodium hydrogen phosphate. In some aspects, the pH modifying agent is citric acid. In some aspects, the pH modifying agent is sodium citrate. In some aspects, the pH modifying agent is sodium hydroxide. In some aspects, the pH modifying agent is sodium dihydrogen phosphate. In some aspects, the pH modifying agent is disodium hydrogen phosphate.

In some aspects, the one or more excipients comprise an emulsifying agent selected from the group consisting of: a polysorbate, cetostearyl alcohol, and cetyl alcohol. In some aspects, the emulsifying agent is a polysorbate. In some aspects, the emulsifying agent is cetostearyl alcohol. In some aspects, the emulsifying agent is cetyl alcohol.

In some aspects, the one or more excipients comprise an antioxidant. In some aspects, the antioxidant is selected from the group consisting of: butylated hydroxyanisole, butylated hydroxytoluene, ascorbic acid, tocopherol, and vitamin E. In some aspects, the antioxidant is butylated hydroxyanisole. In some aspects, the antioxidant is butylated hydroxytoluene. In some aspects, the antioxidant is ascorbic acid. In some aspects, the antioxidant is tocopherol. In some aspects, the antioxidant is vitamin E.

In some aspects, the pharmaceutical composition comprises an antioxidant in an amount of less than 10 wt/wt %. In some aspects, the pharmaceutical composition comprises an antioxidant in an amount of less than 9 wt/wt %. In some aspects, the pharmaceutical composition comprises an antioxidant in an amount of less than 8 wt/wt %. In some aspects, the pharmaceutical composition comprises an antioxidant in an amount of less than 7 wt/wt %. In some aspects, the pharmaceutical composition comprises an antioxidant in an amount of less than 6 wt/wt %. In some aspects, the pharmaceutical composition comprises an antioxidant in an amount of less than 5 wt/wt %. In some aspects, the pharmaceutical composition comprises an antioxidant in an amount of less than 4 wt/wt %. In some aspects, the pharmaceutical composition comprises an antioxidant in an amount of less than 3 wt/wt %. In some aspects, the pharmaceutical composition comprises an antioxidant in an amount of less than 2 wt/wt %. In some aspects, the pharmaceutical composition comprises an antioxidant in an amount of less than 1 wt/wt %.

In some aspects, the pharmaceutical composition comprises an antioxidant in an amount of less than 10 wt/vol %. In some aspects, the pharmaceutical composition comprises an antioxidant in an amount of less than 9 wt/vol %. In some aspects, the pharmaceutical composition comprises an antioxidant in an amount of less than 8 wt/vol %. In some aspects, the pharmaceutical composition comprises an antioxidant in an amount of less than 7 wt/vol %. In some aspects, the pharmaceutical composition comprises an antioxidant in an amount of less than 6 wt/vol %. In some aspects, the pharmaceutical composition comprises an antioxidant in an amount of less than 5 wt/vol %. In some aspects, the pharmaceutical composition comprises an antioxidant in an amount of less than 4 wt/vol %. In some aspects, the pharmaceutical composition comprises an antioxidant in an amount of less than 3 wt/vol %. In some aspects, the pharmaceutical composition comprises an antioxidant in an amount of less than 2 wt/vol %. In some aspects, the pharmaceutical composition comprises an antioxidant in an amount of less than 1 wt/vol %.

In some aspects, the one or more excipients comprise a chelating agent. In some aspects, the chelating agent is ethylenediaminetetraacetic acid. In some aspects, the chelating agent is a disodium salt of ethylenediaminetetraacetic acid.

In some aspects, the one or more excipients comprise a preservative. In some aspects, the preservative is selected from the group consisting of: methyl paraben, ethyl paraben, propyl paraben, butyl paraben, benzoic acid, sodium benzoate, and benzalkonium chloride. In some aspects, the preservative is methyl paraben. In some aspects, the preservative is ethyl paraben. In some aspects, the preservative is propyl paraben. In some aspects, the preservative is butyl paraben. In some aspects, the preservative is benzoic acid. In some aspects, the preservative is sodium benzoate. In some aspects, the preservative is benzalkonium chloride.

In some aspects, the pharmaceutical composition comprises a preservative in an amount of less than 10 wt/wt %. In some aspects, the pharmaceutical composition comprises a preservative in an amount of less than 9 wt/wt %. In some aspects, the pharmaceutical composition comprises a preservative in an amount of less than 8 wt/wt %. In some aspects, the pharmaceutical composition comprises a preservative in an amount of less than 7 wt/wt %. In some aspects, the pharmaceutical composition comprises a preservative in an amount of less than 6 wt/wt %. In some aspects, the pharmaceutical composition comprises a preservative in an amount of less than 5 wt/wt %. In some aspects, the pharmaceutical composition comprises a preservative in an amount of less than 4 wt/wt %. In some aspects, the pharmaceutical composition comprises a preservative in an amount of less than 3 wt/wt %. In some aspects, the pharmaceutical composition comprises a preservative in an amount of less than 2 wt/wt %. In some aspects, the pharmaceutical composition comprises a preservative in an amount of less than 1 wt/wt %.

In some aspects, the pharmaceutical composition comprises a preservative in an amount of less than 10 wt/vol %. In some aspects, the pharmaceutical composition comprises a preservative in an amount of less than 9 wt/vol %. In some aspects, the pharmaceutical composition comprises a preservative in an amount of less than 8 wt/vol %. In some aspects, the pharmaceutical composition comprises a preservative in an amount of less than 7 wt/vol %. In some aspects, the pharmaceutical composition comprises a preservative in an amount of less than 6 wt/vol %. In some aspects, the pharmaceutical composition comprises a preservative in an amount of less than 5 wt/vol %. In some aspects, the pharmaceutical composition comprises a preservative in an amount of less than 4 wt/vol %. In some aspects, the pharmaceutical composition comprises a preservative in an amount of less than 3 wt/vol %. In some aspects, the pharmaceutical composition comprises a preservative in an amount of less than 2 wt/vol %. In some aspects, the pharmaceutical composition comprises a preservative in an amount of less than 1 wt/vol %.

In some aspects, the one or more excipients comprise an antifoaming agent. In some aspects, the pharmaceutical composition comprises an antifoaming agent in an amount of less than 10 wt/wt %. In some aspects, the pharmaceutical composition comprises an antifoaming agent in an amount of less than 9 wt/wt %. In some aspects, the pharmaceutical composition comprises an antifoaming agent in an amount of less than 8 wt/wt %. In some aspects, the pharmaceutical composition comprises an antifoaming agent in an amount of less than 7 wt/wt %. In some aspects, the pharmaceutical composition comprises an antifoaming agent in an amount of less than 6 wt/wt %. In some aspects, the pharmaceutical composition comprises an antifoaming agent in an amount of less than 5 wt/wt %. In some aspects, the pharmaceutical composition comprises an antifoaming agent in an amount of less than 4 wt/wt %. In some aspects, the pharmaceutical composition comprises an antifoaming agent in an amount of less than 3 wt/wt %. In some aspects, the pharmaceutical composition comprises an antifoaming agent in an amount of less than 2 wt/wt %. In some aspects, the pharmaceutical composition comprises an antifoaming agent in an amount of less than 1 wt/wt %.

In some aspects, the one or more excipients comprise an antifoaming agent. In some aspects, the pharmaceutical composition comprises an antifoaming agent in an amount of less than 10 wt/vol %. In some aspects, the pharmaceutical composition comprises an antifoaming agent in an amount of less than 9 wt/vol %. In some aspects, the pharmaceutical composition comprises an antifoaming agent in an amount of less than 8 wt/vol %. In some aspects, the pharmaceutical composition comprises an antifoaming agent in an amount of less than 7 wt/vol %. In some aspects, the pharmaceutical composition comprises an antifoaming agent in an amount of less than 6 wt/vol %. In some aspects, the pharmaceutical composition comprises an antifoaming agent in an amount of less than 5 wt/vol %. In some aspects, the pharmaceutical composition comprises an antifoaming agent in an amount of less than 4 wt/vol %. In some aspects, the pharmaceutical composition comprises an antifoaming agent in an amount of less than 3 wt/vol %. In some aspects, the pharmaceutical composition comprises an antifoaming agent in an amount of less than 2 wt/vol %. In some aspects, the pharmaceutical composition comprises an antifoaming agent in an amount of less than 1 wt/vol %.

In some aspects, the one or more excipients comprise a solubilizer. In some aspects, the solubilizer is cremophor. In some aspects, the solubilizer is vitamin E. In some aspects, the solubilizer is polyethylene glycol. In some aspects, the solubilizer is propylene glycol. In some aspects, the solubilizer comprises a co-solvent.

In some aspects, the one or more excipients comprise a vehicle. In some aspects, the vehicle is selected from the group consisting of: water, ethanol, glycerol, propylene glycol, polyethylene glycol, and an oil. In some aspects, the vehicle is water. In some aspects, the vehicle is ethanol. In some aspects, the vehicle is glycerol. In some aspects, the vehicle is propylene glycol. In some aspects, the vehicle is an oil.

In some aspects, the one or more excipients comprise a surfactant or a wetting agent. In some aspects, the surfactant or wetting agent is selected from the group consisting of: a polysorbate, a polyoxamer, and sodium lauryl sulfate. In some aspects, the surfactant or wetting agent is polysorbate. In some aspects, the surfactant or wetting agent is a polyoxamer. In some aspects, the surfactant or wetting agent is sodium lauryl sulfate.

In some aspects, the one or more excipients comprise a sweetener. In some aspects, the sweetener is selected from the list consisting of: sorbitol, mannitol, xylitol, aspartame, sucralose, saccharine, and acesulfame K. In some aspects, the sweetener is sorbitol. In some aspects, the sweetener is mannitol. In some aspects, the sweetener is xylitol. In some aspects, the sweetener is aspartame. In some aspects, the sweetener is sucralose. In some aspects, the sweetener is saccharine. In some aspects, the sweetener is acesulfame K.

In some aspects, the pharmaceutical composition comprises a sweetener in an amount of less than 10 wt/wt %. In some aspects, the pharmaceutical composition comprises a sweetener in an amount of less than 9 wt/wt %. In some aspects, the pharmaceutical composition comprises a sweetener in an amount of less than 8 wt/wt %. In some aspects, the pharmaceutical composition comprises a sweetener in an amount of less than 7 wt/wt %. In some aspects, the pharmaceutical composition comprises a sweetener in an amount of less than 6 wt/wt %. In some aspects, the pharmaceutical composition comprises a sweetener in an amount of less than 5 wt/wt %. In some aspects, the pharmaceutical composition comprises a sweetener in an amount of less than 4 wt/wt %. In some aspects, the pharmaceutical composition comprises a sweetener in an amount of less than 3 wt/wt %. In some aspects, the pharmaceutical composition comprises a sweetener in an amount of less than 2 wt/wt %. In some aspects, the pharmaceutical composition comprises a sweetener in an amount of less than 1 wt/wt %.

In some aspects, the pharmaceutical composition comprises a sweetener in an amount of less than 10 wt/vol %. In some aspects, the pharmaceutical composition comprises a sweetener in an amount of less than 9 wt/vol %. In some aspects, the pharmaceutical composition comprises a sweetener in an amount of less than 8 wt/vol %. In some aspects, the pharmaceutical composition comprises a sweetener in an amount of less than 7 wt/vol %. In some aspects, the pharmaceutical composition comprises a sweetener in an amount of less than 6 wt/vol %. In some aspects, the pharmaceutical composition comprises a sweetener in an amount of less than 5 wt/vol %. In some aspects, the pharmaceutical composition comprises a sweetener in an amount of less than 4 wt/vol %. In some aspects, the pharmaceutical composition comprises a sweetener in an amount of less than 3 wt/vol %. In some aspects, the pharmaceutical composition comprises a sweetener in an amount of less than 2 wt/vol %. In some aspects, the pharmaceutical composition comprises a sweetener in an amount of less than 1 wt/vol %.

In some aspects, the one or more excipients comprise a stabilizer.

In some aspects, the one or more excipients comprise a flavoring agent. In some aspects, the flavoring agent is selected from the list consisting of: an apple flavoring agent, an orange flavoring agent, a mint flavoring agent, a cherry flavoring agent, and a strawberry flavoring agent. In some aspects, the flavoring agent is an apple flavoring agent. In some aspects, the flavoring agent is an orange flavoring agent. In some aspects, the flavoring agent is a strawberry flavoring agent.

In some aspects, the pharmaceutical composition comprises a flavoring agent in an amount of less than 10 wt/wt %. In some aspects, the pharmaceutical composition comprises a flavoring agent in an amount of less than 9 wt/wt %. In some aspects, the pharmaceutical composition comprises a flavoring agent in an amount of less than 8 wt/wt %. In some aspects, the pharmaceutical composition comprises a flavoring agent in an amount of less than 7 wt/wt %. In some aspects, the pharmaceutical composition comprises a flavoring agent in an amount of less than 6 wt/wt %. In some aspects, the pharmaceutical composition comprises a flavoring agent in an amount of less than 5 wt/wt %. In some aspects, the pharmaceutical composition comprises a flavoring agent in an amount of less than 4 wt/wt %. In some aspects, the pharmaceutical composition comprises a flavoring agent in an amount of less than 3 wt/wt %. In some aspects, the pharmaceutical composition comprises a flavoring agent in an amount of less than 2 wt/wt %. In some aspects, the pharmaceutical composition comprises a flavoring agent in an amount of less than 1 wt/wt %.

In some aspects, the pharmaceutical composition comprises a flavoring agent in an amount of less than 10 wt/vol %. In some aspects, the pharmaceutical composition comprises a flavoring agent in an amount of less than 9 wt/vol %. In some aspects, the pharmaceutical composition comprises a flavoring agent in an amount of less than 8 wt/vol %. In some aspects, the pharmaceutical composition comprises a flavoring agent in an amount of less than 7 wt/vol %. In some aspects, the pharmaceutical composition comprises a flavoring agent in an amount of less than 6 wt/vol %. In some aspects, the pharmaceutical composition comprises a flavoring agent in an amount of less than 5 wt/vol %. In some aspects, the pharmaceutical composition comprises a flavoring agent in an amount of less than 4 wt/vol %. In some aspects, the pharmaceutical composition comprises a flavoring agent in an amount of less than 3 wt/vol %. In some aspects, the pharmaceutical composition comprises a flavoring agent in an amount of less than 2 wt/vol %. In some aspects, the pharmaceutical composition comprises a flavoring agent in an amount of less than 1 wt/vol %.

In some aspects, the one or more excipients comprise a colorant.

Free from Impurities

In some aspects, the pharmaceutical composition is substantially free of impurities.

In some aspects, the pharmaceutical composition comprises less than 5 wt/wt % of all impurities relative to the mass of losartan. In some aspects, the pharmaceutical composition comprises less than 4.5 wt/wt % of all impurities relative to the mass of losartan. In some aspects, the pharmaceutical composition comprises less than 4 wt/wt % of all impurities relative to the mass of losartan. In some aspects, the pharmaceutical composition comprises less than 3.5 wt/wt % of all impurities relative to the mass of losartan. In some aspects, the pharmaceutical composition comprises less than 3 wt/wt % of all impurities relative to the mass of losartan. In some aspects, the pharmaceutical composition comprises less than 2.5 wt/wt % of all impurities relative to the mass of losartan. In some aspects, the pharmaceutical composition comprises less than 2 wt/wt % of all impurities relative to the mass of losartan. In some aspects, the pharmaceutical composition comprises less than 1.5 wt/wt % of all impurities relative to the mass of losartan. In some aspects, the pharmaceutical composition comprises less than 1 wt/wt % of all impurities relative to the mass of losartan. In some aspects, the pharmaceutical composition comprises less than 0.9 wt/wt % of all impurities relative to the mass of losartan. In some aspects, the pharmaceutical composition comprises less than 0.8 wt/wt % of all impurities relative to the mass of losartan. In some aspects, the pharmaceutical composition comprises less than 0.7 wt/wt % of all impurities relative to the mass of losartan. In some aspects, the pharmaceutical composition comprises less than 0.6 wt/wt % of all impurities relative to the mass of losartan. In some aspects, the pharmaceutical composition comprises less than 0.5 wt/wt % of all impurities relative to the mass of losartan. In some aspects, the pharmaceutical composition comprises less than 0.4 wt/wt % of all impurities relative to the mass of losartan. In some aspects, the pharmaceutical composition comprises less than 0.3 wt/wt % of all impurities relative to the mass of losartan. In some aspects, the pharmaceutical composition comprises less than 0.2 wt/wt % of all impurities relative to the mass of losartan. In some aspects, the pharmaceutical composition comprises less than 0.1 wt/wt % of all impurities relative to the mass of losartan. In some aspects, the pharmaceutical composition comprises less than 0.08 wt/wt % of all impurities relative to the mass of losartan. In some aspects, the pharmaceutical composition comprises less than 0.05 wt/wt % of all impurities relative to the mass of losartan. In some aspects, the pharmaceutical composition comprises less than 0.03 wt/wt % of all impurities relative to the mass of losartan. In some aspects, the pharmaceutical composition comprises less than 0.02 wt/wt % of all impurities relative to the mass of losartan. In some aspects, the pharmaceutical composition comprises less than 0.01 wt/wt % of all impurities relative to the mass of losartan.

In some aspects, the pharmaceutical composition comprises less than 5 wt/wt % of an impurity relative to the mass of losartan. In some aspects, the pharmaceutical composition comprises less than 4.5 wt/wt % of an impurity relative to the mass of losartan. In some aspects, the pharmaceutical composition comprises less than 4 wt/wt % of an impurity relative to the mass of losartan. In some aspects, the pharmaceutical composition comprises less than 3.5 wt/wt % of an impurity relative to the mass of losartan. In some aspects, the pharmaceutical composition comprises less than 3 wt/wt % of an impurity relative to the mass of losartan. In some aspects, the pharmaceutical composition comprises less than 2.5 wt/wt % of an impurity relative to the mass of losartan. In some aspects, the pharmaceutical composition comprises less than 2 wt/wt % of an impurity relative to the mass of losartan. In some aspects, the pharmaceutical composition comprises less than 1.5 wt/wt % of an impurity relative to the mass of losartan. In some aspects, the pharmaceutical composition comprises less than 1 wt/wt % of an impurity relative to the mass of losartan. In some aspects, the pharmaceutical composition comprises less than 0.9 wt/wt % of an impurity relative to the mass of losartan. In some aspects, the pharmaceutical composition comprises less than 0.8 wt/wt % of an impurity relative to the mass of losartan. In some aspects, the pharmaceutical composition comprises less than 0.7 wt/wt % of an impurity relative to the mass of losartan. In some aspects, the pharmaceutical composition comprises less than 0.6 wt/wt % of an impurity relative to the mass of losartan. In some aspects, the pharmaceutical composition comprises less than 0.5 wt/wt % of an impurity relative to the mass of losartan. In some aspects, the pharmaceutical composition comprises less than 0.4 wt/wt % of an impurity relative to the mass of losartan. In some aspects, the pharmaceutical composition comprises less than 0.3 wt/wt % of an impurity relative to the mass of losartan. In some aspects, the pharmaceutical composition comprises less than 0.2 wt/wt % of an impurity relative to the mass of losartan. In some aspects, the pharmaceutical composition comprises less than 0.1 wt/wt % of an impurity relative to the mass of losartan. In some aspects, the pharmaceutical composition comprises less than 0.08 wt/wt % of an impurity relative to the mass of losartan. In some aspects, the pharmaceutical composition comprises less than 0.05 wt/wt % of an impurity relative to the mass of losartan. In some aspects, the pharmaceutical composition comprises less than 0.03 wt/wt % of an impurity relative to the mass of losartan. In some aspects, the pharmaceutical composition comprises less than 0.02 wt/wt % of an impurity relative to the mass of losartan. In some aspects, the pharmaceutical composition comprises less than 0.01 wt/wt % of an impurity relative to the mass of losartan.

In some aspect the impurity is a product of losartan oxidation.

In some aspects, the impurity is a product of losartan degradation.

In some aspects, the impurity is a side product of a method of losartan synthesis.

In some aspects, the impurity is a byproduct of a method of losartan synthesis.

In some aspects, the impurity is losartan carboxylic acid.

In some aspects, the impurity is losartan impurity D. In some aspects, the pharmaceutical composition comprises less than 5 wt/wt % of losartan impurity D relative to the mass of losartan. In some aspects, the pharmaceutical composition comprises less than 4.5 wt/wt % of losartan impurity D relative to the mass of losartan. In some aspects, the pharmaceutical composition comprises less than 4 wt/wt % of losartan impurity D relative to the mass of losartan. In some aspects, the pharmaceutical composition comprises less than 3.5 wt/wt % of losartan impurity D relative to the mass of losartan. In some aspects, the pharmaceutical composition comprises less than 3 wt/wt % of losartan impurity D relative to the mass of losartan. In some aspects, the pharmaceutical composition comprises less than 2.5 wt/wt % of losartan impurity D relative to the mass of losartan. In some aspects, the pharmaceutical composition comprises less than 2 wt/wt % of losartan impurity D relative to the mass of losartan. In some aspects, the pharmaceutical composition comprises less than 1.9 wt/wt % of losartan impurity D relative to the mass of losartan. In some aspects, the pharmaceutical composition comprises less than 1.8 wt/wt % of losartan impurity D relative to the mass of losartan. In some aspects, the pharmaceutical composition comprises less than 1.7 wt/wt % of losartan impurity D relative to the mass of losartan. In some aspects, the pharmaceutical composition comprises less than 1.6 wt/wt % of losartan impurity D relative to the mass of losartan. In some aspects, the pharmaceutical composition comprises less than 1.5 wt/wt % of losartan impurity D relative to the mass of losartan. In some aspects, the pharmaceutical composition comprises less than 1.4 wt/wt % of losartan impurity D relative to the mass of losartan. In some aspects, the pharmaceutical composition comprises less than 1.3 wt/wt % of losartan impurity D relative to the mass of losartan. In some aspects, the pharmaceutical composition comprises less than 1.2 wt/wt % of losartan impurity D relative to the mass of losartan. In some aspects, the pharmaceutical composition comprises less than 1.1 wt/wt % of losartan impurity D relative to the mass of losartan. In some aspects, the pharmaceutical composition comprises less than 1 wt/wt % of losartan impurity D relative to the mass of losartan. In some aspects, the pharmaceutical composition comprises less than 0.9 wt/wt % of losartan impurity D relative to the mass of losartan. In some aspects, the pharmaceutical composition comprises less than 0.8 wt/wt % of losartan impurity D relative to the mass of losartan. In some aspects, the pharmaceutical composition comprises less than 0.7 wt/wt % of losartan impurity D relative to the mass of losartan. In some aspects, the pharmaceutical composition comprises less than 0.6 wt/wt % of losartan impurity D relative to the mass of losartan. In some aspects, the pharmaceutical composition comprises less than 0.5 wt/wt % of losartan impurity D relative to the mass of losartan. In some aspects, the pharmaceutical composition comprises less than 0.4 wt/wt % of losartan impurity D relative to the mass of losartan. In some aspects, the pharmaceutical composition comprises less than 0.3 wt/wt % of losartan impurity D relative to the mass of losartan. In some aspects, the pharmaceutical composition comprises less than 0.2 wt/wt % of losartan impurity D relative to the mass of losartan. In some aspects, the pharmaceutical composition comprises less than 0.1 wt/wt % of losartan impurity D relative to the mass of losartan. In some aspects, the pharmaceutical composition comprises less than 0.05 wt/wt % of losartan impurity D relative to the mass of losartan. In some aspects, the pharmaceutical composition comprises less than 0.01 wt/wt % of losartan impurity D relative to the mass of losartan.

In some aspects, the impurity is losartan impurity E. In some aspects, the pharmaceutical composition comprises less than 5 wt/wt % of losartan impurity E relative to the mass of losartan. In some aspects, the pharmaceutical composition comprises less than 4.5 wt/wt % of losartan impurity E relative to the mass of losartan. In some aspects, the pharmaceutical composition comprises less than 4 wt/wt % of losartan impurity E relative to the mass of losartan. In some aspects, the pharmaceutical composition comprises less than 3.5 wt/wt % of losartan impurity E relative to the mass of losartan. In some aspects, the pharmaceutical composition comprises less than 3 wt/wt % of losartan impurity E relative to the mass of losartan. In some aspects, the pharmaceutical composition comprises less than 2.5 wt/wt % of losartan impurity E relative to the mass of losartan. In some aspects, the pharmaceutical composition comprises less than 2 wt/wt % of losartan impurity E relative to the mass of losartan. In some aspects, the pharmaceutical composition comprises less than 1.9 wt/wt % of losartan impurity E relative to the mass of losartan. In some aspects, the pharmaceutical composition comprises less than 1.8 wt/wt % of losartan impurity E relative to the mass of losartan. In some aspects, the pharmaceutical composition comprises less than 1.7 wt/wt % of losartan impurity E relative to the mass of losartan. In some aspects, the pharmaceutical composition comprises less than 1.6 wt/wt % of losartan impurity E relative to the mass of losartan. In some aspects, the pharmaceutical composition comprises less than 1.5 wt/wt % of losartan impurity E relative to the mass of losartan. In some aspects, the pharmaceutical composition comprises less than 1.4 wt/wt % of losartan impurity E relative to the mass of losartan. In some aspects, the pharmaceutical composition comprises less than 1.3 wt/wt % of losartan impurity E relative to the mass of losartan. In some aspects, the pharmaceutical composition comprises less than 1.2 wt/wt % of losartan impurity E relative to the mass of losartan. In some aspects, the pharmaceutical composition comprises less than 1.1 wt/wt % of losartan impurity E relative to the mass of losartan. In some aspects, the pharmaceutical composition comprises less than 1 wt/wt % of losartan impurity E relative to the mass of losartan. In some aspects, the pharmaceutical composition comprises less than 0.9 wt/wt % of losartan impurity E relative to the mass of losartan. In some aspects, the pharmaceutical composition comprises less than 0.8 wt/wt % of losartan impurity E relative to the mass of losartan. In some aspects, the pharmaceutical composition comprises less than 0.7 wt/wt % of losartan impurity E relative to the mass of losartan. In some aspects, the pharmaceutical composition comprises less than 0.6 wt/wt % of losartan impurity E relative to the mass of losartan. In some aspects, the pharmaceutical composition comprises less than 0.5 wt/wt % of losartan impurity E relative to the mass of losartan. In some aspects, the pharmaceutical composition comprises less than 0.4 wt/wt % of losartan impurity E relative to the mass of losartan. In some aspects, the pharmaceutical composition comprises less than 0.3 wt/wt % of losartan impurity E relative to the mass of losartan. In some aspects, the pharmaceutical composition comprises less than 0.2 wt/wt % of losartan impurity E relative to the mass of losartan. In some aspects, the pharmaceutical composition comprises less than 0.1 wt/wt % of losartan impurity E relative to the mass of losartan. In some aspects, the pharmaceutical composition comprises less than 0.05 wt/wt % of losartan impurity E relative to the mass of losartan. In some aspects, the pharmaceutical composition comprises less than 0.01 wt/wt % of losartan impurity E relative to the mass of losartan.

In some aspects, the impurity is a biological contaminant. In some aspects, the impurity is a living biological contaminant. In some aspects, the impurity is a dead biological contaminant. In some aspects, the impurity is a viral contaminant. In some aspects, the impurity is a fungal contaminant. In some aspects, the impurity is a bacterial contaminant. In some aspects, the impurity is a bacterial endotoxin.

In some aspects, the biological contaminant is a replication-competent, metabolically inactive or minimally active biological product. In some aspects, the replication-competent, metabolically inactive or minimally active biological product is a spore.

In some aspects, the impurity is pyrogenic.

In some aspects, the impurity is detectable as visible particulate matter.

Sterility

In some aspects, the pharmaceutical composition has been subjected to a sterilizing treatment. In some aspects, one or more components of the pharmaceutical composition have been subjected to a sterilizing treatment.

In some aspects, the sterilizing treatment comprises filtration. In some aspects, the sterilizing treatment comprises exposure to a high temperature. In some aspects, the sterilizing treatment comprises exposure to a low temperature. In some aspects, the sterilizing treatment comprises application of ultraviolet radiation. In some aspects, the sterilizing treatment is sufficient to kill a living biological contaminant.

Stability

In some aspects, the pharmaceutically acceptable composition is stable as measured by one or more substantially unchanged characteristics after storage, the one or more substantially unchanged characteristics selected from the group consisting of: the concentration of losartan in the pharmaceutical composition; the concentration of an impurity in the pharmaceutical composition; the visual appearance of the pharmaceutical composition; the viscosity of the pharmaceutical composition; the uniformity of the pharmaceutical composition; and the sedimentation rate of the pharmaceutical composition. In some aspects, the one or more substantially unchanged characteristics comprise the concentration of losartan in the pharmaceutical composition. In some aspects, the one or more substantially unchanged characteristics comprise the concentration of an impurity in the pharmaceutical composition. In some aspects, the one or more substantially unchanged characteristics comprise the visual appearance of the pharmaceutical composition. In some aspects, the one or more substantially unchanged characteristics comprise the viscosity of the pharmaceutical composition. In some aspects, the one or more substantially unchanged characteristics comprise the uniformity of the pharmaceutical composition. In some aspects, the one or more substantially unchanged characteristics comprise the sedimentation rate of the pharmaceutical composition.

In some aspects, the pharmaceutical composition is stable at 2° C.-8° C. and ≤65% relative humidity.

In some aspects, the pharmaceutical composition is stable for 1-24 months at 2° C.-8° C. and ≤65% relative humidity. In some aspects, the pharmaceutical composition is stable for 1-18 months at 2° C.-8° C. and ≤65% relative humidity. In some aspects, the pharmaceutical composition is stable for 1-12 months at 2° C.-8° C. and ≤65% relative humidity. In some aspects, the pharmaceutical composition is stable for 1-6 months at 2° C.-8° C. and ≤65% relative humidity. In some aspects, the pharmaceutical composition is stable for 2-6 months at 2° C.-8° C. and ≤65% relative humidity. In some aspects, the pharmaceutical composition is stable for 3-6 months at 2° C.-8° C. and ≤65% relative humidity. In some aspects, the pharmaceutical composition is stable for 4-6 months at 2° C.-8° C. and ≤65% relative humidity. In some aspects, the pharmaceutical composition is stable for 4-7 months at 2° C.-8° C. and ≤65% relative humidity. In some aspects, the pharmaceutical composition is stable for 4-8 months at 2° C.-8° C. and ≤65% relative humidity. In some aspects, the pharmaceutical composition is stable for 4-10 months at 2° C.-8° C. and ≤65% relative humidity. In some aspects, the pharmaceutical composition is stable for 4-12 months at 2° C.-8° C. and ≤65% relative humidity. In some aspects, the pharmaceutical composition is stable for 4-18 months at 2° C.-8° C. and ≤65% relative humidity. In some aspects, the pharmaceutical composition is stable for 4-24 months at 2° C.-8° C. and ≤65% relative humidity. In some aspects, the pharmaceutical composition is stable for 6-8 months at 2° C.-8° C. and ≤65% relative humidity. In some aspects, the pharmaceutical composition is stable for 6-10 months at 2° C.-8° C. and ≤65% relative humidity. In some aspects, the pharmaceutical composition is stable for 6-12 months at 2° C.-8° C. and ≤65% relative humidity. In some aspects, the pharmaceutical composition is stable for 6-18 months at 2° C.-8° C. and ≤65% relative humidity. In some aspects, the pharmaceutical composition is stable for 6-24 months at 2° C.-8° C. and ≤65% relative humidity. In some aspects, the pharmaceutical composition is stable for 18-24 months at 2° C.-8° C. and ≤65% relative humidity. In some aspects, the pharmaceutical composition is stable for 16-26 months at 2° C.-8° C. and ≤65% relative humidity. In some aspects, the pharmaceutical composition is stable for 18-36 months at 2° C.-8° C. and ≤65% relative humidity. In some aspects, the pharmaceutical composition is stable for 18-30 months at 2° C.-8° C. and ≤65% relative humidity.

In some aspects, the pharmaceutical composition is stable for 2 months at 2° C.-8° C. and ≤65% relative humidity. In some aspects, the pharmaceutical composition is stable for 3 months at 2° C.-8° C. and ≤65% relative humidity. In some aspects, the pharmaceutical composition is stable for 4 months at 2° C.-8° C. and ≤65% relative humidity. In some aspects, the pharmaceutical composition is stable for 5 months at 2° C.-8° C. and ≤65% relative humidity. In some aspects, the pharmaceutical composition is stable for 6 months at 2° C.-8° C. and ≤65% relative humidity. In some aspects, the pharmaceutical composition is stable for 7 months at 2° C.-8° C. and ≤65% relative humidity. In some aspects, the pharmaceutical composition is stable for 8 months at 2° C.-8° C. and ≤65% relative humidity. In some aspects, the pharmaceutical composition is stable for 9 months at 2° C.-8° C. and ≤65% relative humidity. In some aspects, the pharmaceutical composition is stable for 10 months at 2° C.-8° C. and ≤65% relative humidity. In some aspects, the pharmaceutical composition is stable for 11 months at 2° C.-8° C. and ≤65% relative humidity. In some aspects, the pharmaceutical composition is stable for 12 months at 2° C.-8° C. and ≤65% relative humidity. In some aspects, the pharmaceutical composition is stable for 16 months at 2° C.-8° C. and ≤65% relative humidity. In some aspects, the pharmaceutical composition is stable for 18 months at 2° C.-8° C. and ≤65% relative humidity. In some aspects, the pharmaceutical composition is stable for 19 months at 2° C.-8° C. and ≤65% relative humidity. In some aspects, the pharmaceutical composition is stable for 20 months at 2° C.-8° C. and ≤65% relative humidity. In some aspects, the pharmaceutical composition is stable for 21 months at 2° C.-8° C. and ≤65% relative humidity. In some aspects, the pharmaceutical composition is stable for 22 months at 2° C.-8° C. and ≤65% relative humidity. In some aspects, the pharmaceutical composition is stable for 23 months at 2° C.-8° C. and ≤65% relative humidity. In some aspects, the pharmaceutical composition is stable for 24 months at 2° C.-8° C. and ≤65% relative humidity. In some aspects, the pharmaceutical composition is stable for 25 months at 2° C.-8° C. and ≤65% relative humidity. In some aspects, the pharmaceutical composition is stable for 26 months at 2° C.-8° C. and ≤65% relative humidity. In some aspects, the pharmaceutical composition is stable for 27 months at 2° C.-8° C. and ≤65% relative humidity. In some aspects, the pharmaceutical composition is stable for 28 months at 2° C.-8° C. and ≤65% relative humidity. In some aspects, the pharmaceutical composition is stable for 29 months at 2° C.-8° C. and ≤65% relative humidity. In some aspects, the pharmaceutical composition is stable for 30 months at 2° C.-8° C. and ≤65% relative humidity. In some aspects, the pharmaceutical composition is stable for 36 months at 2° C.-8° C. and ≤65% relative humidity.

In some aspects, the pharmaceutical composition is stable at 15° C.-25° C. and ≤65% relative humidity.

In some aspects, the pharmaceutical composition is stable for 1-24 months at 15° C.-25° C. and ≤65% relative humidity. In some aspects, the pharmaceutical composition is stable for 1-18 months at 15° C.-25° C. and ≤65% relative humidity. In some aspects, the pharmaceutical composition is stable for 1-12 months at 15° C.-25° C. and ≤65% relative humidity. In some aspects, the pharmaceutical composition is stable for 1-6 months at 15° C.-25° C. and ≤65% relative humidity. In some aspects, the pharmaceutical composition is stable for 2-6 months at 15° C.-25° C. and ≤65% relative humidity. In some aspects, the pharmaceutical composition is stable for 3-6 months at 15° C.-25° C. and ≤65% relative humidity. In some aspects, the pharmaceutical composition is stable for 4-6 months at 15° C.-25° C. and ≤65% relative humidity. In some aspects, the pharmaceutical composition is stable for 4-7 months at 15° C.-25° C. and ≤65% relative humidity. In some aspects, the pharmaceutical composition is stable for 4-8 months at 15° C.-25° C. and ≤65% relative humidity. In some aspects, the pharmaceutical composition is stable for 4-10 months at 15° C.-25° C. and ≤65% relative humidity. In some aspects, the pharmaceutical composition is stable for 4-12 months at 15° C.-25° C. and ≤65% relative humidity. In some aspects, the pharmaceutical composition is stable for 4-18 months at 15° C.-25° C. and ≤65% relative humidity. In some aspects, the pharmaceutical composition is stable for 4-24 months at 15° C.-25° C. and ≤65% relative humidity. In some aspects, the pharmaceutical composition is stable for 6-8 months at 15° C.-25° C. and ≤65% relative humidity. In some aspects, the pharmaceutical composition is stable for 6-10 months at 15° C.-25° C. and ≤65% relative humidity. In some aspects, the pharmaceutical composition is stable for 6-12 months at 15° C.-25° C. and ≤65% relative humidity. In some aspects, the pharmaceutical composition is stable for 6-18 months at 15° C.-25° C. and ≤65% relative humidity. In some aspects, the pharmaceutical composition is stable for 6-24 months at 15° C.-25° C. and ≤65% relative humidity. In some aspects, the pharmaceutical composition is stable for 18-24 months at 15° C.-25° C. and ≤65% relative humidity. In some aspects, the pharmaceutical composition is stable for 16-26 months at 15° C.-25° C. and ≤65% relative humidity. In some aspects, the pharmaceutical composition is stable for 18-36 months at 15° C.-25° C. and ≤65% relative humidity. In some aspects, the pharmaceutical composition is stable for 18-30 months at 15° C.-25° C. and ≤65% relative humidity.

In some aspects, the pharmaceutical composition is stable for 2 months at 15° C.-25° C. and ≤65% relative humidity. In some aspects, the pharmaceutical composition is stable for 3 months at 15° C.-25° C. and ≤65% relative humidity. In some aspects, the pharmaceutical composition is stable for 4 months at 15° C.-25° C. and ≤65% relative humidity.

In some aspects, the pharmaceutical composition is stable for 5 months at 15° C.-25° C. and ≤65% relative humidity. In some aspects, the pharmaceutical composition is stable for 6 months at 15° C.-25° C. and ≤65% relative humidity. In some aspects, the pharmaceutical composition is stable for 7 months at 15° C.-25° C. and ≤65% relative humidity. In some aspects, the pharmaceutical composition is stable for 8 months at 15° C.-25° C. and ≤65% relative humidity. In some aspects, the pharmaceutical composition is stable for 9 months at 15° C.-25° C. and ≤65% relative humidity. In some aspects, the pharmaceutical composition is stable for 10 months at 15° C.-25° C. and ≤65% relative humidity. In some aspects, the pharmaceutical composition is stable for 11 months at 15° C.-25° C. and ≤65% relative humidity. In some aspects, the pharmaceutical composition is stable for 12 months at 15° C.-25° C. and ≤65% relative humidity. In some aspects, the pharmaceutical composition is stable for 16 months at 15° C.-25° C. and ≤65% relative humidity. In some aspects, the pharmaceutical composition is stable for 18 months at 15° C.-25° C. and ≤65% relative humidity. In some aspects, the pharmaceutical composition is stable for 19 months at 15° C.-25° C. and ≤65% relative humidity. In some aspects, the pharmaceutical composition is stable for 20 months at 15° C.-25° C. and ≤65% relative humidity. In some aspects, the pharmaceutical composition is stable for 21 months at 15° C.-25° C. and ≤65% relative humidity. In some aspects, the pharmaceutical composition is stable for 22 months at 15° C.-25° C. and ≤65% relative humidity. In some aspects, the pharmaceutical composition is stable for 23 months at 15° C.-25° C. and ≤65% relative humidity. In some aspects, the pharmaceutical composition is stable for 24 months at 15° C.-25° C. and ≤65% relative humidity. In some aspects, the pharmaceutical composition is stable for 25 months at 15° C.-25° C. and ≤65% relative humidity. In some aspects, the pharmaceutical composition is stable for 26 months at 15° C.-25° C. and ≤65% relative humidity. In some aspects, the pharmaceutical composition is stable for 27 months at 15° C.-25° C. and ≤65% relative humidity. In some aspects, the pharmaceutical composition is stable for 28 months at 15° C.-25° C. and ≤65% relative humidity. In some aspects, the pharmaceutical composition is stable for 29 months at 15° C.-25° C. and ≤65% relative humidity. In some aspects, the pharmaceutical composition is stable for 30 months at 15° C.-25° C. and ≤65% relative humidity. In some aspects, the pharmaceutical composition is stable for 36 months at 15° C.-25° C. and ≤65% relative humidity.

In some aspects, the pharmaceutical composition is stable at 30° C. and ≤65% relative humidity.

In some aspects, the pharmaceutical composition is stable for 1-24 months at 30° C. and ≤65% relative humidity. In some aspects, the pharmaceutical composition is stable for 1-18 months at 30° C. and ≤65% relative humidity. In some aspects, the pharmaceutical composition is stable for 1-12 months at 30° C. and ≤65% relative humidity. In some aspects, the pharmaceutical composition is stable for 1-6 months at 30° C. and ≤65% relative humidity. In some aspects, the pharmaceutical composition is stable for 2-6 months at 30° C. and ≤65% relative humidity. In some aspects, the pharmaceutical composition is stable for 3-6 months at 30° C. and ≤65% relative humidity. In some aspects, the pharmaceutical composition is stable for 4-6 months at 30° C. and ≤65% relative humidity. In some aspects, the pharmaceutical composition is stable for 4-7 months at 30° C. and ≤65% relative humidity. In some aspects, the pharmaceutical composition is stable for 4-8 months at 30° C. and ≤65% relative humidity. In some aspects, the pharmaceutical composition is stable for 4-10 months at 30° C. and ≤65% relative humidity. In some aspects, the pharmaceutical composition is stable for 4-12 months at 30° C. and ≤65% relative humidity. In some aspects, the pharmaceutical composition is stable for 4-18 months at 30° C. and ≤65% relative humidity. In some aspects, the pharmaceutical composition is stable for 4-24 months at 30° C. and ≤65% relative humidity. In some aspects, the pharmaceutical composition is stable for 6-8 months at 30° C. and ≤65% relative humidity. In some aspects, the pharmaceutical composition is stable for 6-10 months at 30° C. and ≤65% relative humidity. In some aspects, the pharmaceutical composition is stable for 6-12 months at 30° C. and ≤65% relative humidity. In some aspects, the pharmaceutical composition is stable for 6-18 months at 30° C. and ≤65% relative humidity. In some aspects, the pharmaceutical composition is stable for 6-24 months at 30° C. and ≤65% relative humidity. In some aspects, the pharmaceutical composition is stable for 18-24 months at 30° C. and ≤65% relative humidity. In some aspects, the pharmaceutical composition is stable for 16-26 months at 30° C. and ≤65% relative humidity. In some aspects, the pharmaceutical composition is stable for 18-36 months at 30° C. and ≤65% relative humidity. In some aspects, the pharmaceutical composition is stable for 18-30 months at 30° C. and ≤65% relative humidity.

In some aspects, the pharmaceutical composition is stable for 2 months at 30° C. and ≤65% relative humidity. In some aspects, the pharmaceutical composition is stable for 3 months at 30° C. and ≤65% relative humidity. In some aspects, the pharmaceutical composition is stable for 4 months at 30° C. and ≤65% relative humidity. In some aspects, the pharmaceutical composition is stable for 5 months at 30° C. and ≤65% relative humidity. In some aspects, the pharmaceutical composition is stable for 6 months at 30° C. and ≤65% relative humidity. In some aspects, the pharmaceutical composition is stable for 7 months at 30° C. and ≤65% relative humidity. In some aspects, the pharmaceutical composition is stable for 8 months at 30° C. and ≤65% relative humidity. In some aspects, the pharmaceutical composition is stable for 9 months at 30° C. and ≤65% relative humidity. In some aspects, the pharmaceutical composition is stable for 10 months at 30° C. and ≤65% relative humidity. In some aspects, the pharmaceutical composition is stable for 11 months at 30° C. and ≤65% relative humidity. In some aspects, the pharmaceutical composition is stable for 12 months at 30° C. and ≤65% relative humidity. In some aspects, the pharmaceutical composition is stable for 16 months at 30° C. and ≤65% relative humidity. In some aspects, the pharmaceutical composition is stable for 18 months at 30° C. and ≤65% relative humidity. In some aspects, the pharmaceutical composition is stable for 19 months at 30° C. and ≤65% relative humidity. In some aspects, the pharmaceutical composition is stable for 20 months at 30° C. and ≤65% relative humidity. In some aspects, the pharmaceutical composition is stable for 21 months at 30° C. and ≤65% relative humidity. In some aspects, the pharmaceutical composition is stable for 22 months at 30° C. and ≤65% relative humidity. In some aspects, the pharmaceutical composition is stable for 23 months at 30° C. and ≤65% relative humidity. In some aspects, the pharmaceutical composition is stable for 24 months at 30° C. and ≤65% relative humidity. In some aspects, the pharmaceutical composition is stable for 25 months at 30° C. and ≤65% relative humidity. In some aspects, the pharmaceutical composition is stable for 26 months at 30° C. and ≤65% relative humidity. In some aspects, the pharmaceutical composition is stable for 27 months at 30° C. and ≤65% relative humidity. In some aspects, the pharmaceutical composition is stable for 28 months at 30° C. and ≤65% relative humidity. In some aspects, the pharmaceutical composition is stable for 29 months at 30° C. and ≤65% relative humidity. In some aspects, the pharmaceutical composition is stable for 30 months at 30° C. and ≤65% relative humidity. In some aspects, the pharmaceutical composition is stable for 36 months at 30° C. and ≤65% relative humidity.

In some aspects, the pharmaceutical composition is stable at 40° C. and 75% relative humidity.

In some aspects, the pharmaceutical composition is stable for 1-24 months at 40° C. and 75% relative humidity. In some aspects, the pharmaceutical composition is stable for 1-18 months at 40° C. and 75% relative humidity. In some aspects, the pharmaceutical composition is stable for 1-12 months at 40° C. and 75% relative humidity. In some aspects, the pharmaceutical composition is stable for 1-6 months at 40° C. and 75% relative humidity. In some aspects, the pharmaceutical composition is stable for 2-6 months at 40° C. and 75% relative humidity. In some aspects, the pharmaceutical composition is stable for 3-6 months at 40° C. and 75% relative humidity. In some aspects, the pharmaceutical composition is stable for 4-6 months at 40° C. and 75% relative humidity. In some aspects, the pharmaceutical composition is stable for 4-7 months at 40° C. and 75% relative humidity. In some aspects, the pharmaceutical composition is stable for 4-8 months at 40° C. and 75% relative humidity. In some aspects, the pharmaceutical composition is stable for 4-10 months at 40° C. and 75% relative humidity. In some aspects, the pharmaceutical composition is stable for 4-12 months at 40° C. and 75% relative humidity. In some aspects, the pharmaceutical composition is stable for 4-18 months at 40° C. and 75% relative humidity. In some aspects, the pharmaceutical composition is stable for 4-24 months at 40° C. and 75% relative humidity. In some aspects, the pharmaceutical composition is stable for 6-8 months at 40° C. and 75% relative humidity. In some aspects, the pharmaceutical composition is stable for 6-10 months at 40° C. and 75% relative humidity. In some aspects, the pharmaceutical composition is stable for 6-12 months at 40° C. and 75% relative humidity. In some aspects, the pharmaceutical composition is stable for 6-18 months at 40° C. and 75% relative humidity. In some aspects, the pharmaceutical composition is stable for 6-24 months at 40° C. and 75% relative humidity. In some aspects, the pharmaceutical composition is stable for 18-24 months at 40° C. and ≤65% relative humidity. In some aspects, the pharmaceutical composition is stable for 16-26 months at 40° C. and ≤65% relative humidity. In some aspects, the pharmaceutical composition is stable for 18-36 months at 40° C. and ≤65% relative humidity. In some aspects, the pharmaceutical composition is stable for 18-30 months at 40° C. and ≤65% relative humidity.

In some aspects, the pharmaceutical composition is stable at 40° C. and 75% relative humidity. In some aspects, the pharmaceutical composition is stable for 2 months at 40° C. and 75% relative humidity. In some aspects, the pharmaceutical composition is stable for 3 months at 40° C. and 75% relative humidity. In some aspects, the pharmaceutical composition is stable for 4 months at 40° C. and 75% relative humidity. In some aspects, the pharmaceutical composition is stable for 5 months at 40° C. and 75% relative humidity. In some aspects, the pharmaceutical composition is stable for 6 months at 40° C. and 75% relative humidity. In some aspects, the pharmaceutical composition is stable for 7 months at 40° C. and 75% relative humidity. In some aspects, the pharmaceutical composition is stable for 8 months at 40° C. and 75% relative humidity. In some aspects, the pharmaceutical composition is stable for 9 months at 40° C. and 75% relative humidity. In some aspects, the pharmaceutical composition is stable for 10 months at 40° C. and 75% relative humidity. In some aspects, the pharmaceutical composition is stable for 11 months at 40° C. and 75% relative humidity. In some aspects, the pharmaceutical composition is stable for 12 months at 40° C. and 75% relative humidity. In some aspects, the pharmaceutical composition is stable for 16 months at 40° C. and 75% relative humidity. In some aspects, the pharmaceutical composition is stable for 18 months at 40° C. and 75% relative humidity. In some aspects, the pharmaceutical composition is stable for 19 months at 40° C. and ≤65% relative humidity. In some aspects, the pharmaceutical composition is stable for 20 months at 40° C. and ≤65% relative humidity. In some aspects, the pharmaceutical composition is stable for 21 months at 40° C. and ≤65% relative humidity. In some aspects, the pharmaceutical composition is stable for 22 months at 40° C. and ≤65% relative humidity. In some aspects, the pharmaceutical composition is stable for 23 months at 40° C. and ≤65% relative humidity. In some aspects, the pharmaceutical composition is stable for 24 months at 40° C. and ≤65% relative humidity. In some aspects, the pharmaceutical composition is stable for 25 months at 40° C. and ≤65% relative humidity. In some aspects, the pharmaceutical composition is stable for 26 months at 40° C. and ≤65% relative humidity. In some aspects, the pharmaceutical composition is stable for 27 months at 40° C. and ≤65% relative humidity. In some aspects, the pharmaceutical composition is stable for 28 months at 40° C. and ≤65% relative humidity. In some aspects, the pharmaceutical composition is stable for 29 months at 40° C. and ≤65% relative humidity. In some aspects, the pharmaceutical composition is stable for 30 months at 40° C. and ≤65% relative humidity. In some aspects, the pharmaceutical composition is stable for 36 months at 40° C. and 75% relative humidity.

Liquid and Powder Forms

In some aspects, the pharmaceutical composition of the present disclosure is a solution, an emulsion, or a suspension. In some aspects, the present disclosure provides for a concentrated form of losartan or a pharmaceutically acceptable salt thereof, which can be combined with a suitable diluent to prepare a pharmaceutical composition described herein. In some aspects, the concentrated form of losartan or a pharmaceutically acceptable salt thereof is selected from the group consisting of: a powder, a plurality of granules, modified losartan, and a concentrated liquid form (e.g., a concentrated solution or a low-volume mixed solid and liquid phase). In some aspects, the concentrated form of losartan or a pharmaceutically acceptable salt thereof can be combined with a suitable diluent to prepare one or more of a solution, a suspension, and an emulsion.

In some aspects, the concentrated form of losartan or a pharmaceutically acceptable salt thereof is combined with the suitable diluent and heated to form a pharmaceutically acceptable composition disclosed herein. In some aspects, the concentrated form of losartan or a pharmaceutically acceptable salt thereof is combined with the suitable diluent and an additional component to form a pharmaceutically acceptable composition disclosed herein. In some aspects, the additional component is a pH modifying agent. In some aspects, the pH modifying agent is an acid. In some aspects, the pH modifying agent is a base.

Solution

In some aspects, the pharmaceutical composition is a solution. In some aspects, the pharmaceutical composition is a solution and the pharmaceutical composition comprises losartan. In some aspects, the pharmaceutical composition is a solution and the pharmaceutical composition comprises a pharmaceutically acceptable salt of losartan. In some aspects, the pharmaceutical composition is a solution and the pharmaceutical composition comprises losartan potassium.

In some aspects, the pharmaceutical composition is a solution comprising losartan substantially dissolved in a pharmaceutically acceptable vehicle. In some aspects, the solution comprises at least 50% of losartan or pharmaceutically acceptable salt thereof in dissolved form. In some aspects, the solution comprises at least 55% of losartan or pharmaceutically acceptable salt thereof in dissolved form. In some aspects, the solution comprises at least 60% of losartan or pharmaceutically acceptable salt thereof in dissolved form. In some aspects, the solution comprises at least 65% of losartan or pharmaceutically acceptable salt thereof in dissolved form. In some aspects, the solution comprises at least 70% of losartan or pharmaceutically acceptable salt thereof in dissolved form. In some aspects, the solution comprises at least 75% of losartan or pharmaceutically acceptable salt thereof in dissolved form. In some aspects, the solution comprises at least 80% of losartan or pharmaceutically acceptable salt thereof in dissolved form. In some aspects, the solution comprises at least 85% of losartan or pharmaceutically acceptable salt thereof in dissolved form. In some aspects, the solution comprises at least 90% of losartan or pharmaceutically acceptable salt thereof in dissolved form. In some aspects, the solution comprises at least 95% of losartan or pharmaceutically acceptable salt thereof in dissolved form. In some aspects, the solution further comprises one or more inactive ingredients selected from the group consisting of: co-solvents, pH modifying agents, surfactants, antioxidants, preservatives, and flavoring agents.

Emulsion

In some aspects, the pharmaceutical composition is an emulsion. In some aspects, the pharmaceutical composition is an emulsion and the pharmaceutical composition comprises losartan. In some aspects, the pharmaceutical composition is an emulsion and the pharmaceutical composition comprises a pharmaceutically acceptable salt of losartan. In some aspects, the pharmaceutical composition is an emulsion and the pharmaceutical composition comprises losartan potassium.

In some aspects, the emulsion is a multiple emulsion. In some aspect, the emulsion is a microemulsion.

In some aspects, the emulsion comprises at least two immiscible liquid phases wherein one liquid phase is in the form of globules. In some aspects, the pharmaceutical composition comprises an emulsifying agent. In some aspects, the pharmaceutical composition is an emulsion wherein a hydrophobic phase comprises at least 50% of losartan or a pharmaceutically acceptable salt thereof. In some aspects, the pharmaceutical composition is an emulsion wherein a hydrophobic phase comprises at least 60% of losartan or a pharmaceutically acceptable salt thereof. In some aspects, the pharmaceutical composition is an emulsion wherein a hydrophobic phase comprises at least 70% of losartan or a pharmaceutically acceptable salt thereof. In some aspects, the pharmaceutical composition is an emulsion wherein a hydrophobic phase comprises at least 80% of losartan or a pharmaceutically acceptable salt thereof. In some aspects, the pharmaceutical composition is an emulsion wherein a hydrophobic phase comprises at least 90% of losartan or a pharmaceutically acceptable salt thereof. In some aspects, the pharmaceutical composition is an emulsion wherein a hydrophobic phase comprises at least 95% of losartan or a pharmaceutically acceptable salt thereof.

Suspension

In some aspects, the pharmaceutical composition is a suspension. In some aspects, the pharmaceutical composition is a suspension and the pharmaceutical composition comprises losartan. In some aspects, the pharmaceutical composition is a suspension and the pharmaceutical composition comprises a pharmaceutically acceptable salt of losartan. In some aspects, the pharmaceutical composition is a suspension and the pharmaceutical composition comprises losartan potassium.

In some aspects, the suspension is a cloudy biphasic liquid comprising a plurality of losartan particles uniformly dispersed in a pharmaceutically acceptable vehicle. In some aspects, at least 50% of losartan or pharmaceutically acceptable salt thereof is in suspended form. In some aspects, at least 60% of losartan or pharmaceutically acceptable salt thereof is in suspended form. In some aspects, at least 70% of losartan or pharmaceutically acceptable salt thereof is in suspended form. In some aspects, at least 80% of losartan or pharmaceutically acceptable salt thereof is in suspended form. In some aspects, at least 90% of losartan or pharmaceutically acceptable salt thereof is in suspended form.

In some aspects, the suspension comprises a flocculating agent.

Powder

In some aspects, the present disclosure provides a powder which is combined with a liquid to produce the pharmaceutical composition described herein.

In some aspects, the powder comprises losartan or a pharmaceutically acceptable form thereof. In some aspects, the powder comprises losartan. In some aspects, the powder comprises losartan potassium.

In some aspects, the powder comprises one or more pharmaceutically acceptable excipients.

In some aspects, the powder is bioequivalent to COZAAR®.

In some aspects, the powder is sterile.

In some aspects, the powder is non-pyrogenic.

In some aspects, the powder is substantially free of impurities.

In some aspects, the liquid is a solvent. In some aspects, the solvent is water.

In some aspects, the liquid is provided in a container. In some aspects, the container is a bottle. In some aspects, the bottle is an amber bottle.

In some aspects, the container contains a suspending agent. In some aspects, the container contains a preservative. In some aspects, the container contains a sweetener. In some aspects, the container contains a flavoring agent.

In some aspects, the powder is packaged in a sachet.

Granules

In some aspects, the present disclosure provides a plurality of granules which is combined with a liquid to produce the pharmaceutical composition described herein.

In some aspects, the plurality of granules comprises losartan or a pharmaceutically acceptable salt thereof. In some aspects, the plurality of granules comprises losartan. In some aspects, the plurality of granules comprises losartan potassium.

In some aspects, the plurality of granules comprises one or more pharmaceutically acceptable excipients.

In some aspects, the plurality of granules is bioequivalent to COZAAR®.

In some aspects, the plurality of granules is sterile.

In some aspects, the plurality of granules is non-pyrogenic.

In some aspects, the plurality of granules is substantially free of impurities.

In some aspects, the liquid is a solvent. In some aspects, the solvent is water.

In some aspects, the liquid is provided in a container. In some aspects, the container is a bottle. In some aspects, the bottle is an amber bottle.

In some aspects, the container contains a suspending agent. In some aspects, the container contains a preservative. In some aspects, the container contains a sweetener. In some aspects, the container contains a flavoring agent.

In some aspects, the plurality of granules is packaged in a sachet.

Particle Characterization

In some aspects, the suspension or the powder exhibits a dissolution profile as measured using a paddle type apparatus. In some aspects, the dissolution profile is measured at 50 rpm. In some aspects, the dissolution profile of the suspension or powder is measured in a mixture of water and 0.1N HCl. In some aspects, less than 35% of the plurality of losartan particles are dissolved in 15 minutes. In some aspects, less than 70% of the plurality of losartan particles are dissolved in 30 minutes. In some aspects, at least 80% of the plurality of losartan particles are dissolved in 60 minutes. In some aspects, at least 80% of the plurality of losartan particles are dissolved in 15 minutes. In some aspects, at least 85% of the plurality of losartan particles are dissolved in 15 minutes. In some aspects, at least 90% of the plurality of losartan particles are dissolved in 15 minutes. In some aspects, at least 95% of the plurality of losartan particles are dissolved in 15 minutes. In some aspects, about 100% of the plurality of losartan particles are dissolved in 15 minutes. In some aspects, at least 80% of the plurality of losartan particles are dissolved in 5 minutes. In some aspects, at least 85% of the plurality of losartan particles are dissolved in 5 minutes. In some aspects, at least 90% of the plurality of losartan particles are dissolved in 5 minutes. In some aspects, at least 95% of the plurality of losartan particles are dissolved in 5 minutes. In some aspects, about 100% of the plurality of losartan particles are dissolved in 5 minutes.

In some aspects, the suspension or powder exhibits a particle size distribution as measured using a particle size analyzer. In some aspects, the particle size analyzer is a Malvern Mastersizer particle size analyzer. In some aspects, the particle size analyzer is a Malvern Mastersizer 3000 particle size analyzer. In some aspects, the particle size analyzer is a Malvern Zetasizer particle size analyzer.

In some aspects, the particle size distribution comprises a D10 value less than 100 μm. In some aspects, the particle size distribution comprises a D50 value less than 500 μm. In some aspects, the particle size distribution comprises a D90 value less than 1000 μm. In some aspects, the particle size distribution comprises a D10 value less than 100 μm, a D50 value less than 500 μm, and a D90 value less than 1000 μm.

In some aspects, the particle size distribution comprises a D10 value less than 20 μm. In some aspects, the particle size distribution comprises a D50 value less than 100 μm. In some aspects, the particle size distribution comprises a D90 value less than 300 μm. In some aspects, the particle size distribution comprises a D10 value less than 20 μm, a D50 value less than 100 μm, and a D90 value less than 300 μm.

In some aspects, the particle size distribution comprises a D10 value less than 2 μm. In some aspects, the particle size distribution comprises a D50 value less than 10 μm. In some aspects, the particle size distribution comprises a D90 value less than 30 μm. In some aspects, the particle size distribution comprises a D10 value less than 2 μm, a D50 value less than 10 μm, and a D90 value less than 30 μm.

In some aspects, the particle size distribution comprises a D10 value less than 100 nm. In some aspects, the particle size distribution comprises a D50 value less than 500 nm. In some aspects, the particle size distribution comprises a D90 value less than 1000 nm. In some aspects, the particle size distribution comprises a D10 value less than 100 nm, a D50 value less than 500 nm, and a D90 value less than 1000 nm.

In some aspects, the particle size distribution comprises a D10 value less than or equal to 1 μm. In some aspects, the particle size distribution comprises a D50 value less than or equal to 5 μm. In some aspects, the particle size distribution comprises a D90 value less than or equal to 15 μm. In some aspects, the particle size distribution comprises a D10 value less than or equal to 1 μm, a D50 value less than or equal to 5 μm, and a D90 value less than or equal to 15 μm.

In some aspects, the particle size distribution comprises a D90 value less than 2 μm. In some aspects, the particle size distribution comprises a D90 value less than 1 μm. In some aspects, the particle size distribution comprises a D90 value less than 500 nm.

In some aspects, the suspension or the powder has a sedimentation rate of less than 10% over a period of 24 hours. In some aspects, the suspension or the powder has a sedimentation rate of less than 5% over a period of 24 hours.

Modified Losartan

In some aspects, the pharmaceutical composition comprises a modified losartan. In some aspects, the powder comprises a modified losartan. In some aspects, the modified losartan comprises losartan or a pharmaceutically acceptable salt thereof complexed or coated with a wax, one or more polymers, or one or more other inactive ingredients. In some aspects, the modified losartan comprises losartan or a pharmaceutically acceptable salt thereof complexed or coated with a wax. In some aspects, the modified losartan comprises losartan or a pharmaceutically acceptable salt thereof complexed or coated with one or more polymers. In some aspects, the modified losartan is losartan or a pharmaceutically acceptable salt thereof coated with one or more inactive ingredients.

Crystalline Form

In some aspects, the powder or suspension comprises losartan or a pharmaceutically acceptable salt thereof in crystalline form. In some aspects, the crystalline form is thermodynamically stable. In some aspects, the crystalline form is thermodynamically stable, as measured by a substantially unchanged X-ray powder diffraction (XRPD) profile following storage. In some aspects, the crystalline form is thermodynamically stable, as measured by a substantially unchanged differential scanning calorimetry (DSC) profile following storage.

Concentration of Losartan

In some aspects, the pharmaceutical composition comprises about 1 mg/mL to about 50 mg/mL of losartan or pharmaceutically acceptable salt thereof. In some aspects, the pharmaceutical composition comprises about 2 mg/mL to about 20 mg/mL of losartan or a pharmaceutically acceptable salt thereof. In some aspects, the pharmaceutical composition comprises about 5 mg/mL to about 20 mg/mL of losartan or a pharmaceutically acceptable salt thereof. In some aspects, the pharmaceutical composition comprises about 8 mg/mL to about 12 mg/mL of losartan or a pharmaceutically acceptable salt thereof.

In some aspects, the pharmaceutical composition comprises about 1 mg/mL of losartan or a pharmaceutically acceptable salt thereof. In some aspects, the pharmaceutical composition comprises about 2 mg/mL of losartan or a pharmaceutically acceptable salt thereof. In some aspects, the pharmaceutical composition comprises about 3 mg/mL of losartan or a pharmaceutically acceptable salt thereof. In some aspects, the pharmaceutical composition comprises about 4 mg/mL of losartan or a pharmaceutically acceptable salt thereof. In some aspects, the pharmaceutical composition comprises about 5 mg/mL of losartan or a pharmaceutically acceptable salt thereof. In some aspects, the pharmaceutical composition comprises about 6 mg/mL of losartan or a pharmaceutically acceptable salt thereof. In some aspects, the pharmaceutical composition comprises about 7 mg/mL of losartan or a pharmaceutically acceptable salt thereof. In some aspects, the pharmaceutical composition comprises about 8 mg/mL of losartan or a pharmaceutically acceptable salt thereof. In some aspects, the pharmaceutical composition comprises about 9 mg/mL of losartan or a pharmaceutically acceptable salt thereof. In some aspects, the pharmaceutical composition comprises about 10 mg/mL of losartan or a pharmaceutically acceptable salt thereof. In some aspects, the pharmaceutical composition comprises about 11 mg/mL of losartan or a pharmaceutically acceptable salt thereof. In some aspects, the pharmaceutical composition comprises about 12 mg/mL of losartan or a pharmaceutically acceptable salt thereof. In some aspects, the pharmaceutical composition comprises about 13 mg/mL of losartan or a pharmaceutically acceptable salt thereof. In some aspects, the pharmaceutical composition comprises about 14 mg/mL of losartan or a pharmaceutically acceptable salt thereof. In some aspects, the pharmaceutical composition comprises about 15 mg/mL of losartan or a pharmaceutically acceptable salt thereof. In some aspects, the pharmaceutical composition comprises about 16 mg/mL of losartan or a pharmaceutically acceptable salt thereof. In some aspects, the pharmaceutical composition comprises about 17 mg/mL of losartan or a pharmaceutically acceptable salt thereof. In some aspects, the pharmaceutical composition comprises about 18 mg/mL of losartan or a pharmaceutically acceptable salt thereof. In some aspects, the pharmaceutical composition comprises about 19 mg/mL of losartan or a pharmaceutically acceptable salt thereof. In some aspects, the pharmaceutical composition comprises about 20 mg/mL of losartan or a pharmaceutically acceptable salt thereof. In some aspects, the pharmaceutical composition comprises about 21 mg/mL of losartan or a pharmaceutically acceptable salt thereof. In some aspects, the pharmaceutical composition comprises about 22 mg/mL of losartan or a pharmaceutically acceptable salt thereof. In some aspects, the pharmaceutical composition comprises about 23 mg/mL of losartan or a pharmaceutically acceptable salt thereof. In some aspects, the pharmaceutical composition comprises about 24 mg/mL of losartan or a pharmaceutically acceptable salt thereof. In some aspects, the pharmaceutical composition comprises about 25 mg/mL of losartan or a pharmaceutically acceptable salt thereof. In some aspects, the pharmaceutical composition comprises about 26 mg/mL of losartan or a pharmaceutically acceptable salt thereof. In some aspects, the pharmaceutical composition comprises about 27 mg/mL of losartan or a pharmaceutically acceptable salt thereof. In some aspects, the pharmaceutical composition comprises about 28 mg/mL of losartan or a pharmaceutically acceptable salt thereof. In some aspects, the pharmaceutical composition comprises about 29 mg/mL of losartan or a pharmaceutically acceptable salt thereof. In some aspects, the pharmaceutical composition comprises about 30 mg/mL of losartan or a pharmaceutically acceptable salt thereof. In some aspects, the pharmaceutical composition comprises about 31 mg/mL of losartan or a pharmaceutically acceptable salt thereof. In some aspects, the pharmaceutical composition comprises about 32 mg/mL of losartan or a pharmaceutically acceptable salt thereof. In some aspects, the pharmaceutical composition comprises about 33 mg/mL of losartan or a pharmaceutically acceptable salt thereof. In some aspects, the pharmaceutical composition comprises about 34 mg/mL of losartan or a pharmaceutically acceptable salt thereof. In some aspects, the pharmaceutical composition comprises about 35 mg/mL of losartan or a pharmaceutically acceptable salt thereof. In some aspects, the pharmaceutical composition comprises about 36 mg/mL of losartan or a pharmaceutically acceptable salt thereof. In some aspects, the pharmaceutical composition comprises about 37 mg/mL of losartan or a pharmaceutically acceptable salt thereof. In some aspects, the pharmaceutical composition comprises about 38 mg/mL of losartan or a pharmaceutically acceptable salt thereof. In some aspects, the pharmaceutical composition comprises about 39 mg/mL of losartan or a pharmaceutically acceptable salt thereof. In some aspects, the pharmaceutical composition comprises about 40 mg/mL of losartan or a pharmaceutically acceptable salt thereof. In some aspects, the pharmaceutical composition comprises about 41 mg/mL of losartan or a pharmaceutically acceptable salt thereof. In some aspects, the pharmaceutical composition comprises about 42 mg/mL of losartan or a pharmaceutically acceptable salt thereof. In some aspects, the pharmaceutical composition comprises about 43 mg/mL of losartan or a pharmaceutically acceptable salt thereof. In some aspects, the pharmaceutical composition comprises about 44 mg/mL of losartan or a pharmaceutically acceptable salt thereof. In some aspects, the pharmaceutical composition comprises about 45 mg/mL of losartan or a pharmaceutically acceptable salt thereof. In some aspects, the pharmaceutical composition comprises about 46 mg/mL of losartan or a pharmaceutically acceptable salt thereof. In some aspects, the pharmaceutical composition comprises about 47 mg/mL of losartan or a pharmaceutically acceptable salt thereof. In some aspects, the pharmaceutical composition comprises about 48 mg/mL of losartan or a pharmaceutically acceptable salt thereof. In some aspects, the pharmaceutical composition comprises about 49 mg/mL of losartan or a pharmaceutically acceptable salt thereof. In some aspects, the pharmaceutical composition comprises about 50 mg/mL of losartan or a pharmaceutically acceptable salt thereof.

pH

In some aspects, the pharmaceutical composition has a pH between 2 and 10. In some aspects, the pharmaceutical composition has a pH between 4 and 7. In some aspects, the pharmaceutical composition has a pH between 1 and 9. In some aspects, the pharmaceutical composition has a pH between 2 and 8. In some aspects, the pharmaceutical composition has a pH between 3 and 7. In some aspects, the pharmaceutical composition has a pH between 4 and 6. In some aspects, the pharmaceutical composition has a pH between 5 and 7. In some aspects, the pharmaceutical composition has a pH between 3 and 5. In some aspects, the pharmaceutical composition has a pH between 7 and 9. In some aspects, the pH is 4.2.

In some aspects, the pharmaceutical composition has a pH less than 10. In some aspects, the pharmaceutical composition has a pH less than 9. In some aspects, the pharmaceutical composition has a pH less than 8. In some aspects, the pharmaceutical composition has a pH less than 7. In some aspects, the pharmaceutical composition has a pH less than 6. In some aspects, the pharmaceutical composition has a pH less than 5. In some aspects, the pharmaceutical composition has a pH less than 4. In some aspects, the pharmaceutical composition has a pH less than 3. In some aspects, the pharmaceutical composition has a pH less than 2.

In some aspects, the pharmaceutical composition has a pH greater than 10. In some aspects, the pharmaceutical composition has a pH greater than 9. In some aspects, the pharmaceutical composition has a pH greater than 8. In some aspects, the pharmaceutical composition has a pH greater than 7. In some aspects, the pharmaceutical composition has a pH greater than 6. In some aspects, the pharmaceutical composition has a pH greater than 5. In some aspects, the pharmaceutical composition has a pH greater than 4. In some aspects, the pharmaceutical composition has a pH greater than 3. In some aspects, the pharmaceutical composition has a pH greater than 2.

In some aspects, the pharmaceutical composition has a pH of about 2. In some aspects, the pharmaceutical composition has a pH of about 2.5. In some aspects, the pharmaceutical composition has a pH of about 3. In some aspects, the pharmaceutical composition has a pH of about 3.5. In some aspects, the pharmaceutical composition has a pH of about 4. In some aspects, the pharmaceutical composition has a pH of about 4.1. In some aspects, the pharmaceutical composition has a pH of about 4.2. In some aspects, the pharmaceutical composition has a pH of about 4.3. In some aspects, the pharmaceutical composition has a pH of about 4.4. In some aspects, the pharmaceutical composition has a pH of about 4.5. In some aspects, the pharmaceutical composition has a pH of about 5. In some aspects, the pharmaceutical composition has a pH of about 5.5. In some aspects, the pharmaceutical composition has a pH of about 6. In some aspects, the pharmaceutical composition has a pH of about 6.5. In some aspects, the pharmaceutical composition has a pH of about 7. In some aspects, the pharmaceutical composition has a pH of about 7.5. In some aspects, the pharmaceutical composition has a pH of about 8. In some aspects, the pharmaceutical composition has a pH of about 8.5. In some aspects, the pharmaceutical composition has a pH of about 9. In some aspects, the pharmaceutical composition has a pH of about 9.5. In some aspects, the pharmaceutical composition has a pH of about 10.

In some aspects, the pharmaceutical composition has a pH of 2. In some aspects, the pharmaceutical composition has a pH of 2.5. In some aspects, the pharmaceutical composition has a pH of 3. In some aspects, the pharmaceutical composition has a pH of 3.5. In some aspects, the pharmaceutical composition has a pH of 4. In some aspects, the pharmaceutical composition has a pH of 4.1. In some aspects, the pharmaceutical composition has a pH of 4.2. In some aspects, the pharmaceutical composition has a pH of 4.3. In some aspects, the pharmaceutical composition has a pH of 4.4. In some aspects, the pharmaceutical composition has a pH of 4.5. In some aspects, the pharmaceutical composition has a pH of 5. In some aspects, the pharmaceutical composition has a pH of 5.5. In some aspects, the pharmaceutical composition has a pH of 6. In some aspects, the pharmaceutical composition has a pH of 6.5. In some aspects, the pharmaceutical composition has a pH of 7. In some aspects, the pharmaceutical composition has a pH of 7.5. In some aspects, the pharmaceutical composition has a pH of 8. In some aspects, the pharmaceutical composition has a pH of 8.5. In some aspects, the pharmaceutical composition has a pH of 9. In some aspects, the pharmaceutical composition has a pH of 9.5. In some aspects, the pharmaceutical composition has a pH of 10.

Pharmacokinetic Parameters and Bioequivalence

In some aspects, the mean $T_{max}$ of the pharmaceutical composition described herein is about 98% to about 102% of the mean $T_{max}$ of COZAAR®.

In some aspects, the mean $T_{max}$ of the pharmaceutical composition described herein is about 95% to about 105% of the mean $T_{max}$ of COZAAR®.

In some aspects, the mean $T_{max}$ of the pharmaceutical composition described herein is about 90% to about 110% of the mean $T_{max}$ of COZAAR®.

In some aspects, the mean $T_{max}$ of the pharmaceutical composition described herein is about 80% to about 125% of the mean $T_{max}$ of COZAAR®.

In some aspects, the mean $T_{max}$ of the pharmaceutical composition described herein is about 75% to about 130% of the mean $T_{max}$ of COZAAR®.

In some aspects, the mean $T_{max}$ of the pharmaceutical composition described herein is about 70% to about 135% of the mean $T_{max}$ of COZAAR®.

In some aspects, the mean $T_{max}$ of the pharmaceutical composition described herein is about 65% to about 140% of the mean $T_{max}$ of COZAAR®.

In some aspects, the mean $T_{max}$ of the pharmaceutical composition described herein is about 60% to about 145% of the mean $T_{max}$ of COZAAR®.

In some aspects, the mean $T_{max}$ of the pharmaceutical composition described herein is about 60%, about 65%, about 70%, about 75%, about 80%, about 85%, about 90%, about 95%, about 100%, about 105%, about 110%, about 115%, about 120% about 125%, about 130%, about 135%, about 140%, or about 145% of the mean $T_{max}$ of COZAAR®.

In some aspects, the mean $T_{max}$ of the pharmaceutical composition described herein is about 50% to about 150% of the mean $T_{max}$ of COZAAR®. In some aspects, the mean $T_{max}$ of the pharmaceutical composition described herein is about 40% to about 160% of the mean $T_{max}$ of COZAAR®. In some aspects, the mean $T_{max}$ of the pharmaceutical composition described herein is about 30% to about 170% of the mean $T_{max}$ of COZAAR®. In some aspects, the mean $T_{max}$ of the pharmaceutical composition described herein is about 20% to about 200% of the mean $T_{max}$ of COZAAR®.

In some aspects, the mean $C_{max}$ of the pharmaceutical composition described herein is about 98% to about 102% of the mean $C_{max}$ of COZAAR®.

In some aspects, the mean $C_{max}$ of the pharmaceutical composition described herein is about 95% to about 105% of the mean $C_{max}$ of COZAAR®.

In some aspects, the mean $C_{max}$ of the pharmaceutical composition described herein is about 90% to about 110% of the mean $C_{max}$ of COZAAR®.

In some aspects, the mean $C_{max}$ of the pharmaceutical composition described herein is about 80% to about 125% of the mean $C_{max}$ of COZAAR®.

In some aspects, the mean $C_{max}$ of the pharmaceutical composition described herein is about 75% to about 130% of the mean $C_{max}$ of COZAAR®.

In some aspects, the mean $C_{max}$ of the pharmaceutical composition described herein is about 70% to about 135% of the mean $C_{max}$ of COZAAR®.

In some aspects, the mean $C_{max}$ of the pharmaceutical composition described herein is about 65% to about 140% of the mean $C_{max}$ of COZAAR®.

In some aspects, the mean $C_{max}$ of the pharmaceutical composition described herein is about 60% to about 145% of the mean $C_{max}$ of COZAAR®.

In some aspects, the mean $C_{max}$ of the pharmaceutical composition described herein is about 60%, about 65%, about 70%, about 75%, about 80%, about 85%, about 90%, about 95%, about 100%, about 105%, about 110%, about 115%, about 120% about 125%, about 130%, about 135%, about 140%, or about 145% of the mean $C_{max}$ of COZAAR®.

In some aspects, the mean $AUC_{0-\infty}$ of the pharmaceutical composition described herein is about 98% to about 102% of the mean $AUC_{0-\infty}$ of COZAAR®.

In some aspects, the mean $AUC_{0-\infty}$ of the pharmaceutical composition described herein is about 95% to about 105% of the mean $AUC_{0-\infty}$ of COZAAR®.

In some aspects, the mean $AUC_{0-\infty}$ of the pharmaceutical composition described herein is about 90% to about 110% of the mean $AUC_{0-\infty}$ of COZAAR®.

In some aspects, the mean $AUC_{0-\infty}$ of the pharmaceutical composition described herein is about 80% to about 125% of the mean $AUC_{0-\infty}$ of COZAAR®.

In some aspects, the mean $AUC_{0-\infty}$ of the pharmaceutical composition described herein is about 75% to about 130% of the mean $AUC_{0-\infty}$ of COZAAR®.

In some aspects, the mean $AUC_{0-\infty}$ of the pharmaceutical composition described herein is about 70% to about 135% of the mean $AUC_{0-\infty}$ of COZAAR®.

In some aspects, the mean $AUC_{0-\infty}$ of the pharmaceutical composition described herein is about 65% to about 140% of the mean $AUC_{0-\infty}$ of COZAAR®.

In some aspects, the mean $AUC_{0-\infty}$ of the pharmaceutical composition described herein is about 60% to about 145% of the mean $AUC_{0-\infty}$ of COZAAR®.

In some aspects, the mean $AUC_{0-\infty}$ of the pharmaceutical composition described herein is about 60%, about 65%, about 70%, about 75%, about 80%, about 85%, about 90%, about 95%, about 100%, about 105%, about 110%, about 115%, about 120% about 125%, about 130%, about 135%, about 140%, or about 145% of the mean $AUC_{0-\infty}$ of COZAAR®.

Additional Active Ingredients

In some aspects, the pharmaceutical composition comprises one or more active ingredients in addition to losartan or a pharmaceutically acceptable salt thereof. In some aspects, the one or more active ingredients are selected from the group consisting of: calcium channel blockers, diuretics, ACE inhibitors, and beta blockers. In some aspects, the one or more active ingredients are calcium channel blockers. In some aspects, the one or more active ingredients are diuretics. In some aspects, the one or more active ingredients are ACE inhibitors. In some aspects, the one or more active ingredients are beta blockers.

Viscosity

In some aspects, the pharmaceutical composition has a viscosity of less than 2000 centipoise, as measured using a Brookfield viscometer. In some aspects, the pharmaceutical composition has a viscosity of less than 1000 centipoise, as measured using a Brookfield viscometer. In some aspects, the pharmaceutical composition has a viscosity of about 100 to 2000 centipoise, as measured using a Brookfield viscometer. In some aspects, the pharmaceutical composition has a viscosity of about 100 to 1500 centipoise, as measured using a Brookfield viscometer. In some aspects, the pharmaceutical composition has a viscosity of about 100 to 1000 centipoise, as measured using a Brookfield viscometer. In some aspects, the pharmaceutical composition has a viscosity of about 500 to 2000 centipoise, as measured using a Brookfield viscometer. In some aspects, the pharmaceutical composition has a viscosity of about 100 to 2500 centipoise, as measured using a Brookfield viscometer.

Volume

In some aspects, the pharmaceutical composition is administered in a volume of 0.5 mL to 50 mL. In some aspects, the pharmaceutical composition is administered in a volume of less than 100 mL. In some aspects, the pharmaceutical composition is administered in a volume of less than 90 mL. In some aspects, the pharmaceutical composition is administered in a volume of less than 80 mL. In some aspects, the pharmaceutical composition is administered in a volume of less than 70 mL. In some aspects, the pharmaceutical composition is administered in a volume of less than 60 mL. In some aspects, the pharmaceutical composition is administered in a volume of less than 50 mL. In some aspects, the pharmaceutical composition is administered in a volume of less than 40 mL. In some aspects, the pharmaceutical composition is administered in a volume of less than 30 mL. In some aspects, the pharmaceutical composition is administered in a volume of less than 20 mL. In some aspects, the pharmaceutical composition is administered in a volume of less than 10 mL. In some aspects, the pharmaceutical composition is administered in a volume of less than 5 mL.

In some aspects, the pharmaceutical composition is administered in a volume of about 0.1 mL, about 0.2 mL, about 0.3 mL, about 0.4 mL, about 0.5 mL, about 0.7 mL, about 0.8 mL, about 0.9 mL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, about 2 mL, about 2.1 mL, about 2.2 mL, about 2.3 mL, about 2.4 mL, about 2.5 mL, about 3 mL, about 3.5 mL, about 4 mL, about 4.5 mL, about 5 mL, about 5.5 mL, about 6 mL, about 6.5 mL, about 7 mL, about 7.5 mL, about 8 mL, about 8.5 mL, about 9 mL, about 9.5 mL, or about 10 mL.

In some aspects, the pharmaceutical composition is administered in a volume of about 0.1 mL to about 20 mL, about 0.1 mL to about 15 mL, about 0.1 mL to about 10 mL, about 0.1 mL to about 2.5 mL, about 0.5 mL to about 2.5 mL, about 1 mL to about 10 mL, about 1 mL to about 2.5 mL, about 2 mL to about 10 mL, about 2 mL to about 3 mL, about 4 mL to about 6 mL, or about 9 mL to about 11 mL. In some aspects, the pharmaceutical composition is administered in a volume of about 2.5 mL to about 10 mL.

Container

In some aspects, a pharmaceutical composition is packaged in a glass container. In some aspects, the powder is packaged in a glass container. In some aspects, the glass container is an amber glass container. In some aspects, the amber glass container is child resistant. In some aspects, the amber glass container comprises a child resistant cap. In some aspects, the pharmaceutical composition is packaged in a polymeric container. In some aspects, the polymeric container is child resistant. In some aspects, the polymeric container comprises a child resistant cap. In some aspects, the polymeric container comprises high density polyethylene (HDPE). In some aspects, the polymeric container comprises low density polyethylene (LDPE).

Kit

In some aspects, the present disclosure provides for a kit comprising a pharmaceutically acceptable composition described herein, and further comprising a set of instructions for administration of the pharmaceutically acceptable composition to a subject in need thereof. In some aspects, the set of instructions comprises an instruction to add an amount of a diluent to a container comprising a concentrated form of losartan or a pharmaceutically acceptable salt thereof, wherein the kit comprises the container. In some aspects, the diluent is water.

In some aspects, the present disclosure provides for a kit comprising: a concentrated form of losartan or a pharmaceutically acceptable salt thereof; a diluent; and a set of instructions, wherein the set of instructions comprises: instructions for combining the concentrated form of losartan or a pharmaceutically acceptable salt thereof and the diluent to form a pharmaceutically acceptable composition described herein; and instructions for administration of the pharmaceutically acceptable composition to a subject in need thereof. In some aspects, the concentrated form of losartan is in the form of a powder or a plurality of granules. In some aspects, the concentrated form of losartan or a pharmaceutically acceptable salt thereof is in the form of a powder. In some aspects, the concentrated form of losartan or a pharmaceutically acceptable salt thereof is in the form of a plurality of granules.

In some aspects, the kit comprises a concentrated form of a pharmaceutical composition disclosed herein. In some aspects, the concentrated form is prepared by combining components of a pharmaceutical composition disclosed herein without dilution to a final concentration suitable for administration to a subject. In some aspects, the concentrated form is a concentrated liquid form. In some aspects, the concentrated liquid form is a solution. In some aspects, the concentrated liquid form is a suspension. In some aspects, the concentrated form is a dry form. In some aspects, the dry form comprises less than 0.1%, 0.5%, 1%, 2%, 3%, 4%, 5%, 6%, 7%, 8%, 9%, or 10% of water by weight of the dry form. In some aspects, the dry form is a powder or a plurality of granules.

Method of Preparing Suspension

In some aspects, the present disclosure provides a method of preparing a suspension described herein, the method comprising combining a plurality of losartan particles and a suspending agent. In some aspects, the plurality of losartan particles is combined with the suspending agent.

In some aspects, the present disclosure provides a method of preparing a suspension described herein, the method comprising dissolving losartan or a pharmaceutically acceptable salt thereof in a suitable fluid (e.g., water), adjusting the pH of the suitable liquid comprising losartan or a pharmaceutically acceptable salt thereof, and combining the suitable liquid comprising losartan or a pharmaceutically acceptable salt thereof with the remaining components of the suspension, thereby forming the suspension.

In some aspects, the present disclosure provides a method of preparing a suspension described herein, the method comprising combining losartan or a pharmaceutically acceptable salt thereof and one or more excipients, granulating the composition with a suitable fluid (e.g., water), drying the resulting composition to form a dry composition, and combining the dry composition with a suitable liquid, thereby forming the suspension.

In some aspects, the present disclosure provides a method of preparing a suspension described herein, the method comprising a step of particle size reduction. In some aspects, the step of particle size reduction comprises wet milling. In some aspects, the step of particle size reduction comprises microfluidation. In some aspects, the step of particle size reduction comprises homogenization. In some aspects, the step of particle size reduction comprises nano-milling.

In some aspects, a pH modifying agent is added after the plurality of losartan particles is combined with the suspending agent. In some aspects, the pH modifying agent is selected from the group consisting of citric acid, sodium citrate, acetic acid, sodium acetate, sodium hydroxide, dibasic calcium phosphate, sodium dihydrogen phosphate, and disodium hydrogen phosphate. In some aspects, the pH modifying agent is a buffer.

In some aspects, the one or more polymers are sprayed by dissolving the one or more polymers in a volatile solvent. In some aspects, the volatile solvent is selected from the group consisting of: ethanol, acetone, or isopropyl alcohol. In some aspects, the volatile solvent is ethanol. In some aspects, the volatile solvent is acetone. In some aspects, the volatile solvent is isopropyl alcohol.

In some aspects, heated air is added to cause evaporation of the volatile solvent. In some aspects, evaporation of the volatile solvent causes deposition of the one or more polymers onto the surface of a particle comprising losartan or a pharmaceutically acceptable salt thereof. In some aspects, the particles comprising losartan or a pharmaceutically acceptable salt thereof are dried to form a modified losartan. In some aspects, the plurality of losartan particles is provided as a modified losartan which is preformed. In some aspects, the plurality of losartan particles comprises losartan or a pharmaceutically acceptable salt thereof.

In some aspects, the plurality of losartan particles are fluidized in a fluidized bed system, and are then coated with one or more polymers. In some aspects, the plurality of losartan particles comprises losartan or a pharmaceutically acceptable salt thereof. In some aspects, the plurality of losartan particles has a particle size of less than 1000 μm. In some aspects, the plurality of losartan particles has a particle size of less than 950 μm. In some aspects, the plurality of losartan particles has a particle size of less than 900 μm. In some aspects, the plurality of losartan particles has a particle size of less than 850 μm. In some aspects, the plurality of losartan particles has a particle size of less than 800 μm. In some aspects, the plurality of losartan particles has a particle size of less than 750 μm. In some aspects, the plurality of losartan particles has a particle size of less than 700 μm. In some aspects, the plurality of losartan particles has a particle size of less than 650 μm. In some aspects, the plurality of losartan particles has a particle size of less than 600 μm. In some aspects, the plurality of losartan particles has a particle size of less than 550 μm. In some aspects, the plurality of losartan particles has a particle size of less than 500 μm. In some aspects, the plurality of losartan particles has a particle size of less than 450 μm. In some aspects, the plurality of losartan particles has a particle size of less than 400 μm. In some aspects, the plurality of losartan particles has a particle size of less than 350 μm. In some aspects, the plurality of losartan particles has a particle size of less than 300 μm. In some aspects, the plurality of losartan particles has a particle size of less than 250 μm. In some aspects, the plurality of losartan particles has a particle size of less than 200 μm. In some aspects, the plurality of losartan particles has a particle size of less than 150 μm. In some aspects, the plurality of losartan particles has a particle size of less than 100 μm. In some aspects, the plurality of losartan particles has a particle size of less than 50 μm.

In some aspects, the one or more polymers comprise pH dependent polymers (e.g., Eudragit L, Eudragit S, or cellulose acetate phthalate) and/or pH independent polymers (e.g., Eudragit RS, Eudragit RL, or cellulose acetate). In some aspects, the one or more polymers comprise pH dependent polymers (e.g., Eudragit L, Eudragit S, or cellulose acetate phthalate). In some aspects, the one or more polymers comprise Eudragit L. In some aspects, the one or more polymers comprise Eudragit S. In some aspects, the one or more polymers comprise cellulose acetate phthalate. In some aspects, the one or more polymers comprise pH independent polymers (e.g., Eudragit RS, Eudragit RL, or cellulose acetate). In some aspects, the one or more polymers comprise Eudragit RS. In some aspects, the one or more polymers comprise Eudragit RL. In some aspects, the one or more polymers comprise cellulose acetate.

In some aspects, the modified losartan tastes less bitter than losartan.

In some aspects, the modified losartan is more stable than losartan.

Method of Preparing Solution or Emulsion

In some aspects, the present disclosure provides a method of preparing a solution or an emulsion described herein, comprising combining the components of the solution or the emulsion.

In some aspects, losartan or a pharmaceutically acceptable salt thereof is dissolved in a hydrophobic phase (e.g., vegetable oil). In some aspects, an antioxidant is added to a hydrophobic phase. In some aspects, the hydrophobic phase comprising losartan or a pharmaceutically acceptable salt thereof is mixed with a hydrophilic phase. In some aspects, the hydrophilic phase comprises a sweetener. In some aspects, the hydrophilic phase comprises a flavoring agent. In some aspects, the hydrophilic phase comprises Polysorbate 80 and/or Tweens. In some aspects, the emulsion is prepared by combining and mixing the hydrophobic phase and the hydrophilic phase. In some aspects, the hydrophobic phase and hydrophilic phase are mixed at a high speed using a homogenizer.

Method of Preparing Powder

In some aspects, the present disclosure provides a method of preparing a powder, the method comprising dry blending the components of a pharmaceutical composition described herein. In some aspects, the pharmaceutical composition is a suspension described herein.

Method of Preparing Modified Losartan

In some aspects, the present disclosure provides a method of preparing modified losartan, the method comprising complexing or coating losartan or a pharmaceutically acceptable salt thereof with a substance, wherein the substance is a wax, a polymer, or one or more other inactive ingredients. In some aspects, the modified losartan is formed during preparation of the pharmaceutical composition. In some aspects, modified losartan is formed by complexation with an ion exchange resin. In some aspects, modified losartan is formed by complexation with a cyclodextrin. In some aspects, the modified losartan is prepared by microencapsulation of losartan or a pharmaceutically acceptable salt thereof in a coat of inactive ingredients.

Method of Treatment

In some aspects, the present disclosure provides a method of treating a subject in need thereof comprising administering to the subject a therapeutically effective amount of the pharmaceutical composition described herein.

In some aspects, the present disclosure provides a method of treating hypertension in a subject in need thereof comprising administering to the subject a therapeutically effective amount of the pharmaceutical composition described herein. In some aspects, the present disclosure provides a method of treating adult hypertension in a subject in need thereof comprising administering to the subject a therapeutically effective amount of the pharmaceutical composition described herein. In some aspects, the present disclosure provides a method of treating pediatric hypertension in a subject in need thereof comprising administering to the subject a therapeutically effective amount of the pharmaceutical composition described herein. In some aspects, the present disclosure provides a method of treating hypertension in a subject in need thereof comprising administering to the subject a therapeutically effective amount of the pharmaceutical composition described herein wherein the subject is a patient with left ventricular hypertrophy. In some aspects, the present disclosure provides a method of treating nephropathy in a subject in need thereof comprising administering to the subject a therapeutically effective amount of the pharmaceutical composition described herein. In some aspects, the present disclosure provides a method of treating nephropathy in a subject in need thereof comprising administering to the subject a therapeutically effective amount of the pharmaceutical composition described herein wherein the subject is a patient with type 2 diabetes.

In some aspects, the subject has been diagnosed with pre-hypertension or hypertension. In some aspects, the subject has been diagnosed with pre-hypertension. In some aspects, the subject has been diagnosed with hypertension. In some aspects, the subject has a history of hypertension.

In some aspects, the subject has been diagnosed with left ventricular hypertrophy. In some aspects, the subject has been diagnosed with both hypertension and left ventricular hypertrophy.

In some aspects, the subject has been diagnosed with type 2 diabetes.

In some aspects, the subject has been diagnosed with nephropathy.

In some aspects, the subject has been diagnosed with diabetic nephropathy.

In some aspects, the subject has been diagnosed with proteinuria.

In some aspects, the subject exhibits a urinary albumin to creatinine ratio of greater than or equal to 300 mg/g.

In some aspects, the subject has been diagnosed with an elevated serum creatinine.

In some aspects, the pharmaceutical composition is co-administered with at least one other pharmaceutical agent. In some aspects, the at least one pharmaceutical agent is an antihypertensive agent. In some aspects, the antihypertensive agent is selected from the group consisting of: an angiotensin II antagonist, an angiotensin converting enzyme inhibitor, or a neutral endopeptidase/angiotensin converting enzyme inhibitor. In some aspects, the antihypertensive agent is an angiotensin II antagonist. In some aspects, the antihypertensive agent is an angiotensin converting enzyme inhibitor. In some aspects, the antihypertensive agent is a neutral endopeptidase/angiotensin converting enzyme inhibitor.

Having described the invention with reference to the different aspects of the invention, other aspects will become apparent to one skilled in the art from consideration of the specification.

The innovation is further defined by reference to the following examples. It will be apparent to those skilled in the art that many modifications to the composition may be practiced without departing from the scope of this invention.

EXAMPLES

In non-limiting examples, pharmaceutical compositions of losartan and methods of producing the same are disclosed herein. Examples 1, 2, 6, and 13 and the Tables 1, 2, 5, and 12 therein shows alternatives for formulation of an oral suspension of losartan. Example 3 provides a method of producing the oral suspension of Example 2, and Example 14 provides a method of producing the suspension of Example 13. Examples 4, 5, and 10-12, and Tables 3, 4, and 9-11 therein provide oral liquid solutions of losartan. Examples 7-9 and Tables 6-8 therein provide powder compositions suitable for reconstitution to prepare a solution (Example 7 and 8) or a suspension (Example 9).

Example 1: Suspension 1

A suspension of losartan suitable for oral administration was prepared having ingredients in the following proportions:

TABLE 1

Losartan Suspension for Oral Administration
Losartan Potassium Oral Suspension, 10 mg/mL

| INGREDIENT | Composition Qty/100 mL |
|---|---|
| purified water, USP | 80-100 g |
| methylparaben, NF | 0.1-0.3 g |
| propylparaben, NF | 0.01-0.03 g |
| losartan potassium, USP | 0.5-1.5 g |
| hydroxyethyl cellulose (NATROSOL ™ 250 L), NF | 1-1.4 g |
| Xanthan gum, NF (XANTURAL ® 180) | 0.5-1.5 g |
| microcrystalline cellulose and carboxymethylcellulose sodium, NF (AVICEL ® RC-591) | 1-2 g |
| disodium edetate, NF | 0.1-0.2 g |
| simethicone emulsion 30%, USP (Q7-2587 simethicone emulsion 30%, USP) | 0.8-1.2 g |
| a flavoring agent | 5-15 mg |
| sucralose micronized, NF (SPLENDA ®) | 0.2-0.6 g |
| anhydrous citric acid, USP | Qs to desired pH (5% citric acid solution in purified water) |

Example 2: Suspension 2

A suspension of losartan suitable for oral administration was prepared having ingredients in the following proportions:

TABLE 2

Losartan Suspension for Oral Administration
Losartan Potassium Oral Suspension, 10 mg/mL

| ITEM NO. | INGREDIENT | Composition Qty/100 mL pH-4.2 | pH-5.0 |
|---|---|---|---|
| 1 | purified water, USP | 80-100 g | 80-100 g |
| 2 | methylparaben, NF | 0.1-0.3 g | 0.18 g |
| 3 | propylparaben, NF | 0.02 g | 0.02 g |
| 4 | losartan potassium, USP | 1.000 g | 1.000 g |
| 5 | hydroxyethyl cellulose (NATROSOL ™ 250 L), NF | 1.20 g | 1.20 g |

TABLE 2-continued

Losartan Suspension for Oral Administration
Losartan Potassium Oral Suspension, 10 mg/mL

| ITEM NO. | INGREDIENT | Composition Qty/100 mL pH-4.2 | pH-5.0 |
|---|---|---|---|
| 6 | Xanthan gum, NF (XANTURAL ® 180) | 0.10 g | 0.10 g |
| 7 | microcrystalline cellulose and carboxymethylcellulose sodium, NF (AVICEL ® RC-591) | 1.50 g | 1.50 g |
| 8 | disodium edetate, NF | 0.15 g | 0.15 g |
| 9 | simethicone emulsion 30%, USP (Q7-2587 simethicone emulsion 30%, USP) | 1.00 g | 1.00 g |
| 10 | sucralose micronized, NF (SPLENDA ®) | 0.40 g | 0.40 g |
| 11 | anhydrous citric acid, USP | Qs to adjust pH (5% citric acid solution with purified water) | |
| 12 | flavoring agent | 5-15 mg | |

Example 3: Method of Producing Suspension of Example 2

1. Preservatives (methylparaben, NF and propylparaben, NF) were dissolved in purified water at a temperature 80-85° C. Once dissolved, the content was cooled to 25° C.
2. Losartan (losartan potassium, USP) was added to the above solution once the temperature was between 25-30° C. and the drug was dissolved in water with preservatives.
3. A 5% citric acid solution was added with continuous homogenizing in an amount such that the final pH of the composition after all components were added would be the desired pH (here, either 4.2 or 5.0).
4. The viscosity modifying agents/thickening agents/suspending agents (hydroxyethyl cellulose (NATROSOL™ 250 L), NF and xanthan gum, NF (XANTURAL© 180)) were added to the composition of step 2 using high shear mixing.
5. Disodium edetate and simethicone emulsion 30% were added to the composition of step 4.
6. Sweetener was added and the composition was mixed for a few minutes.
7. A flavoring agent was added.
8. Qs to batch volume with purified water and composition was mixed.

In some aspects, the pH modifying agent (here, citric acid in step 3) is added after any other step.

Example 4: Losartan Solution

A solution of losartan suitable for oral administration was prepared having ingredients in the following proportions:

TABLE 3

Losartan Solution for Oral Administration
Losartan Potassium Oral Solution, 10 mg/mL

| ITEM NO. | INGREDIENTS | Composition Qty/100 mL | |
|---|---|---|---|
| 1 | purified water, USP | 90.00 g | 90.00 g |
| 2 | methylparaben, NF | 0.18 g | 0.18 g |
| 3 | propylparaben, NF | 0.02 g | 0.02 g |
| 4 | losartan potassium, USP | 1.000 g | 1.000 g |

TABLE 3-continued

| Losartan Solution for Oral Administration<br>Losartan Potassium Oral Solution, 10 mg/mL | | | |
|---|---|---|---|
| ITEM NO. | INGREDIENTS | Composition Qty/100 mL | |
| 5 | hydroxyethyl cellulose (NATROSOL ™ 250 L), NF | 1.20 g | 1.20 g |
| 8 | disodium edetate, NF | 0.15 g | 0.15 g |
| 10 | sucralose micronized, (NF SPLENDA ®) | 0.40 g | 0.40 g |
| 11 | NaOH | Qs to adjust pH >6 | |

Losartan Potassium was dissolved in water and mixed with the rest of the ingredients. The pH was adjusted to 6 using a Sodium Hydroxide solution.

Example 5: Losartan Solution

A solution of losartan suitable for oral administration was prepared having ingredients in the following proportions:

TABLE 4

| Losartan solution for oral administration | | |
|---|---|---|
| No | Ingredients | Formula Quantity (g/100 mL) |
| 1. | Polyethylene Glycol 400, NF | 2.5 g |
| 2. | Propylene glycol, USP | 2.5 g |
| 3. | Methylparaben, NF | 0.18 g |
| 4. | Propylparaben, NF | 0.02 g |
| 5. | Sodium Phosphate, Monobasic USP | 0.114 g |
| 6. | Sodium Phosphate, Dibasic USP | 0.144 g |
| 7. | Losartan Potassium, USP | 1.00 g |
| 8. | Povidone, NF (Kollidon 90F) | 1.00 g |
| 9. | Hypromellose 2910, USP (Methocel E50 Premium LV) | 2.0 g |
| 10. | Xanthan gum, NF | 0.10 g |
| 11. | Purified Water USP | QS |

Polyethylene glycol and Propylene Glycol were mixed, and Methylparaben and Propyl Paraben were added to the mixture to make the preservative phase. Phosphate buffer was prepared using Monobasic and Dibasic Sodium Phosphate. Losartan Potassium was dissolved in water. The preservative phase and buffer phase (monobasic and dibasic sodium phosphate) were then added to make a clear solution. The remaining Ingredients were added with constant mixing using a homogenizer.

Example 6: Losartan Suspension

A suspension of losartan suitable for oral administration was prepared having ingredients in the following proportions:

TABLE 5

| Losartan suspension for oral administration: | | |
|---|---|---|
| No | Ingredients | Quantity (g/100 mL) |
| 1. | Polyethylene Glycol 400, NF | 2.5 g |
| 2. | Propylene glycol, USP | 2.5 g |
| 3. | Methylparaben, NF | 0.18 g |
| 4. | Propylparaben, NF | 0.02 g |
| 5. | Anhydrous Citric Acid, USP | 5.0 g |
| 6. | Vitamin E Polyethylene Glycol Succinate, NF | 2.0 g |
| 7. | Losartan Potassium, USP | 1.00 g |

TABLE 5-continued

| Losartan suspension for oral administration: | | |
|---|---|---|
| No | Ingredients | Quantity (g/100 mL) |
| 8. | Povidone, NF (Kollidon 90F) | 1.0 g |
| 9. | Hypromellose 2910, USP (Methocel E50 Premium LV) | 1.0 g |
| 10. | Microcrystalline Cellulose & Carboxymethylcellulose Sodium, NF (Avicel RC-591) | 1.0 g |
| 11. | Simethicone Emulsion, USP 30% | 1.0 g |
| 12. | Purified Water USP | QS |

Polyethylene glycol and Propylene Glycol were mixed, and Methylparaben and Propyl Paraben were added to the mixture.
Phosphate buffer was prepared using Monobasic and Dibasic Sodium Phosphate.
Citric acid was added to water to a 5% final concentration.
Losartan Potassium was dissolved in water. The 5% citric acid solution was added to dissolve a portion of the API and adjust pH to 4.2.
The preservative phase and buffer phase were added.
The remaining Ingredients were added with constant mixing using a homogenizer. Citric acid was used to adjust the solution to a final pH of 4.2.

Example 7: Losartan Powder for Solution

A solution of losartan suitable for oral administration was prepared from a composition having ingredients in the following proportions:

TABLE 6

| Losartan solution for oral administration | | | |
|---|---|---|---|
| Sr. # | Ingredients | % w/w | gm/100 ml |
| 1 | Losartan Potassium | 33.33 | 1 |
| 2 | Sodium Benzoate | 1.67 | 0.05 |
| 3 | Sodium Citrate | 3.33 | 0.1 |
| 4 | Xanthan Gum | 1.67 | 0.05 |
| 6 | Citric acid | 1.67 | 0.05 |
| 7 | Sucralose | 1.67 | 0.05 |
| 8 | Sorbitol | 56.67 | 1.7 |

Ingredients 1-8 were mixed, then passed through a sieve having a mesh size of 20 (“20 #”), and further mixed using a blender. The resulting mixture can be combined with a suitable diluent to prepare a solution with is administrable as a pharmaceutical composition.

Example 8: Losartan Powder for Solution

A solution of losartan suitable for oral administration was prepared from a composition having ingredients in the following proportions:

TABLE 7

| Losartan solution for oral administration | | | |
|---|---|---|---|
| Sr. # | Ingredients | % w/w | gm/100 ml |
| 1 | Losartan Potassium | 33.33 | 1 |
| 2 | Potassium sorbate | 1.00 | 0.03 |
| 4 | Xanthan Gum | 1.67 | 0.05 |
| 6 | Dibasic Sodium/Calcium phosphate | 1.67 | 0.05 |
| 7 | Sucralose | 1.00 | 0.03 |
| 8 | Sorbitol | 61.33 | 1.84 |

Ingredients 1-8 were mixed, then passed through a 20 #sieve, and further mixed using a blender. The resulting mixture can be combined with a suitable diluent to prepare a solution with is administrable as a pharmaceutical composition.

Example 9: Losartan Powder for Suspension

A suspension of losartan suitable for oral administration was prepared from a composition having ingredients in the following proportions:

TABLE 8

Losartan Powder for oral administration

| Sr. # | Ingredients | mg |
|---|---|---|
| 1 | Losartan Potassium | 100 |
| 2 | Microcrystalline Cellulose | 105 |
| 3 | Lactose Monohydrate | 51 |
| 4 | Pregelatinized Starch 1500 | 41.9 |
| 5 | magnesium Stearate | 2.1 |
| 6 | Citric Acid | 0.75 |
| 7 | Sodium Citrate | 1 |
| 8 | Sucralose | 0.5 |
| 9 | Sorbitol | 97.75 |
| 10 | Xanthum gum | 5 |

Ingredients 1-10 were mixed and passed through a 20 #sieve, then further mixed using a rapid granulator. The powder mix was granulated with water and allowed to dry until the LOD was below 1%. The resulting mixture can be combined with a suitable diluent or suspending agent to prepare a suspension with is administrable as a pharmaceutical composition. For example, 40.5 mg of the mixture, which contains 10 mg of losartan, can be reconstituted in water to prepare a suitable dosage form.

Example 10: Losartan Solution

A solution of losartan suitable for oral administration was prepared having ingredients in the following proportions:

TABLE 9

Losartan solution for oral administration

| Sr. # | Ingredients | % w/w | gm/100 ml |
|---|---|---|---|
| 1 | Losartan Potassium | 2.35 | 1 |
| 2 | Sodium Benzoate | 0.47 | 0.2 |
| 3 | Glycerine | 94.71 | 40.25 |
| 4 | Xanthan Gum | 0.59 | 0.25 |
| 5 | PVK K 30 | 0.71 | 0.3 |
| 6 | Sucralose | 1.18 | 0.5 |

Losartan Potassium was dissolved in water, and the remaining excipients were added with constant stirring using a homogenizer.

Example 11: Losartan Solution

A solution of losartan suitable for oral administration was prepared having ingredients in the following proportions:

TABLE 10

Losartan solution for oral administration

| Sr. # | Ingredient | g/1000 mL |
|---|---|---|
| 1 | Losartan Potassium, USP | 10 g |
| 2 | PEG 400 | 25 g |
| 3 | Propylene Glycol | 25 g |
| 4 | Monobasic sodium phosphate (anhydrous) | 0.57 |
| 5 | Dibasic sodium phosphate (dried) | 0.72 |
| 6 | Methyl Paraben | 1.8 g |
| 7 | Propyl Paraben | 0.2 g |
| 8 | Purified Water | QS to 1000 mL |

Polyethylene glycol and Propylene Glycol were mixed, and Methylparaben and Propyl Paraben were added to the mixture to make the preservative phase. Phosphate buffer was prepared using Monobasic and Dibasic Sodium Phosphate. Losartan Potassium was dissolved in water. The preservative phase and buffer phase (monobasic and dibasic sodium phosphate) were then added to make a clear solution. Add purified water to total volume.

Example 12: Losartan Solution

A solution of losartan suitable for oral administration was prepared having ingredients in the following proportions:

TABLE 11

Losartan solution for oral administration

| Sr. # | Ingredient | g/1000 mL |
|---|---|---|
| 1 | Losartan Potassium, USP | 10 g |
| 2 | Monobasic sodium phosphate (anhydrous) | 0.57 |
| 3 | Dibasic sodium phosphate (dried) | 0.72 |
| 4 | Methyl Paraben | 1.8 g |
| 5 | Propyl Paraben | 0.2 g |
| 6 | Water | q.s. to 1000 ml |

Preservatives (methylparaben, NF and propylparaben, NF) were dissolved in purified water at a temperature 80-85° C. Once dissolved, the content was cooled to 25° C.

Losartan (losartan potassium, USP) was added to the above solution once the temperature was between 25-30° C. and the drug was dissolved in water with preservatives.

Phosphate buffer was prepared using Monobasic and Dibasic Sodium Phosphate and added to the above solution.

Add purified water to total volume.

Example 13: Losartan Suspension

A suspension of losartan suitable for oral administration was prepared having ingredients in the following proportions:

TABLE 12

| Losartan suspension for oral administration | |
|---|---|
| Ingredient | Per 100 mL |
| Losartan Potassium, USP | 1.00 g |
| Methylparaben, NF | 0.18 g |
| Propylparaben, NF | 0.02 g |
| Purified Water, USP (q.s.) | 85.00 g + q.s. |
| Hydroxyethyl cellulose, NF (Natrosol 250 L Pharm) | 1.2 g |
| Xanthan Gum, NF (Xantural 180) | 0.10 g |
| Microcrystalline Cellulose and Carboxymethyl cellulose Sodium, NF (Avicel RC-591) | 1.5 g |
| Edetate Disodium, USP | 0.15 g |
| Simethicone Emulsion 30% USP (Q7-2587 Simethicone Emulsion 30% USP) | 1.00 g |
| Sucralose, NF (Splenda ®, Micronized (Powder) | 0.40 g |
| Monobasic Sodium phosphate (anhydrous) | 0.114 g |
| Disodium Phosphate (dried) | 0.144 g |

Example 14: Method of Producing Suspension of Example 13

Preservatives (methylparaben, NF and propylparaben, NF) were dissolved in purified water at a temperature 80-85° C. Once dissolved, the content was cooled to 25° C.

Losartan (losartan potassium, USP) was added to the above solution once the temperature was between 25-30° C. and the drug was dissolved in water with preservatives.

Phosphate buffer was prepared using Monobasic and Dibasic Sodium Phosphate and added to the above solution.

The viscosity modifying agents/thickening agents/suspending agents (hydroxyethyl cellulose (NATROSOL™ 250 L), NF and xanthan gum, NF (XANTURAL© 180)) were added to the composition of step 2 using high shear mixing.

Disodium edetate and simethicone emulsion 30% were added to the composition of step 4.

Sweetener was added and the composition was mixed for a few minutes.

Qs to batch volume with purified water and composition was mixed.

Example 15: Analysis of Losartan Formulations Administered to Rabbits 60 male New Zealand white rabbits were split into Groups 1 to 6 of 10 random rabbits each.

5 mg of losartan potassium was administered orally to Group 1 as the formulation of Example 11 (a solution).

5 mg of losartan potassium was administered orally to Group 2 as the formulation of Example 12 (a solution).

5 mg of losartan potassium was administered orally to Group 3 as the formulation of Example 6 (a suspension).

5 mg of losartan potassium was administered orally to Group 4 as the formulation of Example 2 (a suspension).

5 mg of losartan potassium was administered orally to Group 5 as the formulation of Example 13 (a suspension).

5 mg of losartan potassium was administered orally to Group 6 as a suspension of COZAAR® prepared according to the instructions provided in COZAAR® label.

Figure 2:
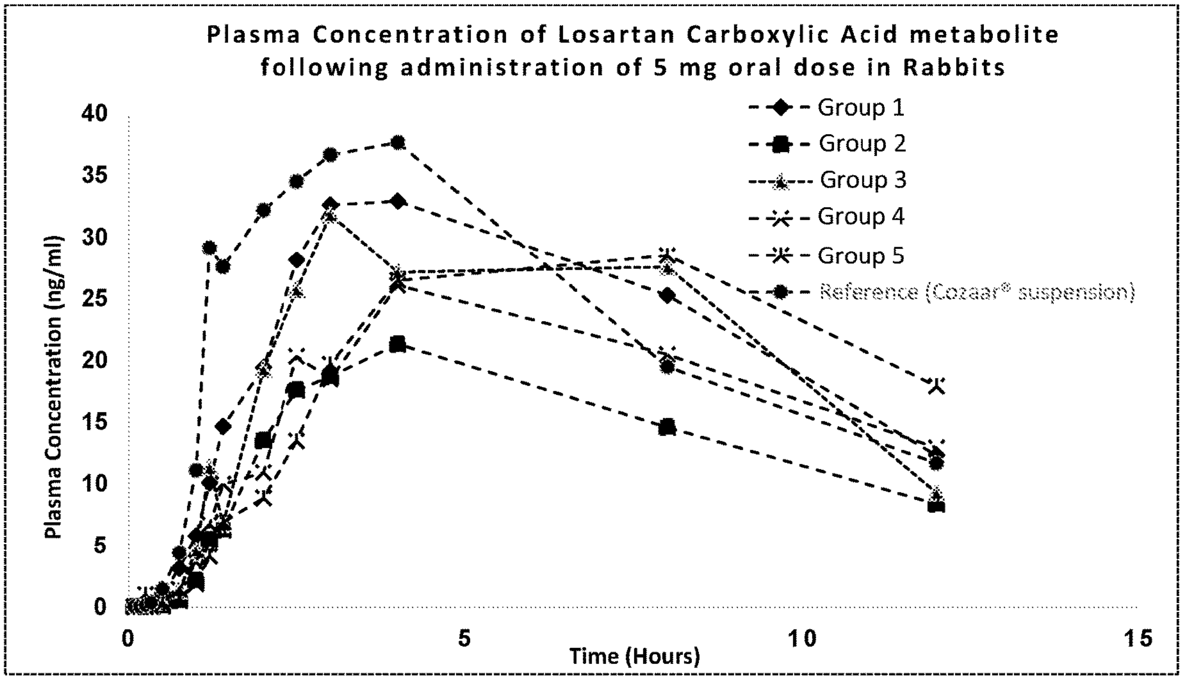
FIG. 2 shows the plasma concentration of losartan carboxylic acid metabolite following administration of 5 mg oral dose losartan potassium in rabbits, as described in Example 15. Corresponding losartan carboxylic acid pharmacokinetic parameters are summarized in Table 14.

The plasma concentration of losartan over time following administration is depicted in FIG. 1. The plasma concentration of losartan carboxylic acid over time following administration is depicted in FIG. 2. Losartan carboxylic acid is a losartan metabolite. FIG. 1 demonstrates that all the administered formulations provide a therapeutically effective concentration of losartan over a period of at least ten hours. Multiple test formulations have a comparable $C_{max}$ and AUC to that of the COZAAR® suspension.

Pharmacokinetic parameters for losartan are presented in Table 13 for each of the Groups 1 to 6. Average values are presented.

TABLE 13

| Losartan Pharmacokinetic Parameters | | | | | | |
|---|---|---|---|---|---|---|
| | Group 1 (solution) | Group 2 (solution) | Group 3 (suspension) | Group 4 (suspension) | Group 5 (suspension) | Group 6 (compounded suspension; COZAAR ®) |
| $C_{max}$ (ng/ml) | 181.05 | 173.73 | 212.11 | 93.78 | 57.03 | 205.76 |
| $AUC_{0\text{-}24\ hr}$ (ng · h/ml) | 630.43 | 539.14 | 772.02 | 577.95 | 401.31 | 712.05 |
| $AUC_{0\text{-}\infty}$ (ng · h/ml) | 763.32 | 682.8 | 976.0 | 902.8 | 528.7 | 880.5 |
| $T_{max}$ (h) | 0.17 | 2.5 | 2.35 | 4 | 4 | 2 |
| $T_{1/2}$ (h) | 4.53 | 3.51 | 4.81 | 5.58 | 5.23 | 3.41 |

The formulations of Groups 1 and 3 resulted in a $C_{max}$ and an $AUC_{0\text{-}\infty}$ between about 80% to about 125% of the $C_{max}$ and an $AUC_{0\text{-}\infty}$ for COZAAR® compounded suspension (Group 6). The formulation of Group 2 resulted in a $C_{max}$ between about 80% to about 125% of the $C_{max}$ of COZAAR® suspension but an $AUC_{0\text{-}\infty}$ less than 80% of the $AUC_{0\text{-}\infty}$ of COZAAR® suspension. The formulation of Group 4 resulted in an $AUC_{0\text{-}\infty}$ between about 80% to about 125% of the $AUC_{0\text{-}\infty}$ of COZAAR® suspension, but an $C_{max}$ less than 80% of the $C_{max}$ of COZAAR® suspension. The formulation of Group 5 resulted in a $C_{max}$ and an $AUC_{0\text{-}\infty}$ below 80% of the $C_{max}$ and an $AUC_{0\text{-}\infty}$ for COZAAR® suspension.

TABLE 14

Losartan Carboxylic Acid Pharmacokinetic Parameters
Pharmacokinetic parameters for losartan carboxylic acid are presented in Table 14 for each of the Groups 1 to 6. Average values are presented.

| | Group 1 (solution) | Group 2 (solution) | Group 3 (suspension) | Group 4 (suspension) | Group 5 (suspension) | Group 6 (compounded suspension; COZAAR ®) |
|---|---|---|---|---|---|---|
| $C_{max}$ (ng/ml) | 39.17 | 23.65 | 45.60 | 34.86 | 32.88 | 50.76 |
| $AUC_{0\text{-}24\ hr}$ (ng · h/ml) | 267.27 | 162.73 | 250.30 | 209.43 | 245.43 | 278.64 |
| $T_{max}$ (h) | 4 | 4 | 3.5 | 4 | 6 | 4 |

The data demonstrates that the test formulations of Groups 1-5 result in the pharmacokinetic profile of losartan metabolite comparable to that of COZAAR® suspension (Group 6).

Example 16: Dissolution, Impurity, and Stability Analysis for the Formulation of Group 4

The formulation of Group 4 was tested for the presence of losartan Impurity D and losartan Impurity E under various conditions. As used in the Examples herein, "ACC" refers to accelerated conditions, in which the formulation was placed at 40° C. and 75% relative humidity (RH). "INT" refers to intermediate conditions, in which the formulation is placed at 30° C. and 65% RH. "CRT" refers to controlled room temperature, in which the formulation is placed at 25° C. and 60% RH.

TABLE 15

Analysis of the Formulation of Group 4 Under Various Conditions

| Test | Initial | 1 Month ACC | 1 Month IRT | 1 Month CRT | 2 Month INT | 2 Month ACC |
|---|---|---|---|---|---|---|
| Assay for Losartan Potassium | 100.3% | 99.8% | 99.8% | 99.4% | 99.9% | 100.2 |
| Related Substances: | | | | | | |
| Impurity D | ND | ND | ND | ND | ND | ND |
| Impurity E | ND | ND | ND | ND | ND | ND |
| Dissolution in 30 mins | 102.8% | 100.6% | 100.1% | 99.7% | 101.5% | 102.0% |

ND: None detected

As Table 15 shows, the formulation of Group 4 retained over 99% of losartan potassium over all conditions tested, indicating purity and stability of the formulation. No Impurity D or Impurity E were detected under any of the conditions tested, further indicating both purity and stability of the losartan formulation. The same dissolution profile was observed in all conditions, further demonstrating stability. No color change was observed over time, further indicating purity and stability.

Example 17: Impurity and Stability Analysis for the Formulation of Group 5

The formulation of Group 5 was tested for the presence of losartan Impurity D and losartan Impurity E under various conditions. Data are presented as wt/wt % relative to the theoretical initial amount of losartan potassium, which corresponds to about 10 mg/mL losartan.

TABLE 16

Analysis of the Formulation of Group 5 Under Various Conditions

| Test | Initial | 20 days CRT | 1 Month CRT | 3 Month CRT | 3 Month ACC |
|---|---|---|---|---|---|
| Assay for losartan potassium | 102.1% | 98.7 | 97.6 | 102.3 | 98 |
| Losartan Impurity D | ND | ND | ND | ND | ND |
| Losartan Impurity E | ND | ND | ND | ND | 0.07 |

ND: None detected

As Table 16 shows, the formulation of Group 5 retained at least 98% of losartan under all conditions tested, indicating stability and purity. Impurity D was not detectable and Impurity E was less than 0.1% wt/wt under all conditions tested, further indicating stability and purity.

Example 18: Impurity and Stability Analysis for the Formulation of Example 5

The formulation of Example 5 was tested for the presence of losartan Impurity D and losartan Impurity E under various conditions. Data are presented as wt/wt % relative to the theoretical initial amount of losartan potassium.

TABLE 17

Analysis of the Formulation Example 5 Under Various Conditions

| Test | Initial | 48 days CRT |
|---|---|---|
| Assay for losartan potassium | 99.50% | 99.90% |
| Losartan Impurity D | ND | ND |
| Losartan Impurity E | ND | ND |

ND: None detected

As Table 17 shows, the formulation of Example 5 retained over 99% of losartan under all conditions tested, indicating stability and purity. Impurity D was not detectable and Impurity E was less than the limits of quantification after 48 days at room temperature, further indicating stability and purity.

What is claimed is:

1. A method of treating hypertension comprising administering to a human in need thereof an oral pharmaceutical composition comprising:

about 10 mg/mL of losartan or a pharmaceutically acceptable salt thereof, a suspending agent selected from the group consisting of hydroxyethylcellulose, methylcellulose, hydroxymethylcellulose, hydroxypropylmethylcellulose, microcrystalline cellulose, sodium carboxymethylcellulose, xanthan gum, acacia, an alginate, and guar gum, or a combination thereof;

a pH modifying agent;

a preservative; and a solubilizer, wherein the pharmaceutical composition is a liquid suspension, and wherein the liquid suspension has a pH of about 7.

2. The method of claim 1, wherein the oral pharmaceutical composition further comprises one or more pharmaceutically acceptable excipients selected from the group consisting of an emulsifying agent, an antioxidant, a chelating agent, a surfactant or wetting agent, a sweetener, a stabilizer, a flavoring agent, and a colorant.

3. The method of claim 1, wherein the oral pharmaceutical composition further comprises crystallization inhibitor.

4. The method of claim 1, wherein the pharmaceutically acceptable salt is losartan potassium.

5. The method of claim 1, wherein the oral pharmaceutical composition further comprises PEG 400, propylene glycol, or both.

6. The method of claim 1, wherein the preservative comprises methyl paraben, propyl paraben, or both.

7. The method of claim 1, wherein the pH modifying agent comprises sodium phosphate monobasic, sodium phosphate dibasic, or both.

8. The method of claim 1, wherein the flavoring agent comprises a mint flavor.

9. The method of claim 1, wherein the suspending agent comprises xanthan gum.

10. The method of claim 1, wherein the oral pharmaceutical composition further comprises an anti-foaming agent.

11. A method of treating nephropathy comprising administering to a human in need thereof an oral pharmaceutical composition comprising:

about 10 mg/mL of losartan or a pharmaceutically acceptable salt thereof, a suspending agent selected from the group consisting of hydroxyethylcellulose, methylcellulose, hydroxymethylcellulose, hydroxypropylmethylcellulose, microcrystalline cellulose, sodium carboxymethylcellulose, xanthan gum, acacia, an alginate, and guar gum, or a combination thereof;

a pH modifying agent;

a preservative; and a solubilizer, wherein the pharmaceutical composition is a liquid suspension, and wherein the liquid suspension has a pH of about 7.

12. The method of claim 11, wherein the oral pharmaceutical composition further comprises one or more pharmaceutically acceptable excipients selected from the group consisting of an emulsifying agent, an antioxidant, a chelating agent, a surfactant or wetting agent, a sweetener, a stabilizer, a flavoring agent, and a colorant.

13. The method of claim 11, wherein the suspending agent comprises xanthan gum.

14. The method of claim 11, wherein the pharmaceutically acceptable salt is losartan potassium.

15. The method of claim 11, wherein the oral pharmaceutical composition further comprises PEG 400, propylene glycol, or both.

16. The method of claim 11, wherein the preservative comprises methyl paraben, propyl paraben, or both.

17. The method of claim 11, wherein the pH modifying agent comprises sodium phosphate monobasic, sodium phosphate dibasic, or both.

18. The method of claim 11, wherein the oral pharmaceutical composition further comprises a crystallization inhibitor.

19. The method of claim 11, wherein the oral pharmaceutical composition further comprises an anti-foaming agent.

20. A method of treating hypertension or diabetic nephropathy comprising administering to a human in need thereof an oral pharmaceutical composition comprising:

about 10 mg/mL of losartan potassium, a suspending agent selected from the group consisting of hydroxyethylcellulose, methylcellulose, hydroxymethylcellulose, hydroxypropylmethylcellulose, microcrystalline cellulose, sodium carboxymethylcellulose, xanthan gum, acacia, an alginate, and guar gum, or a combination thereof;

a pH modifying agent;

a preservative;

a solubilizer;

an emulsifying agent; and a crystallization inhibitor, wherein the pharmaceutical composition is a liquid suspension, and wherein the liquid suspension has a pH of about 7.

* * * * *